(12) United States Patent
Mathieu

(10) Patent No.: US 8,594,388 B2
(45) Date of Patent: Nov. 26, 2013

(54) LARGE DEPTH-OF-FIELD IMAGING SYSTEM AND IRIS RECOGNITON SYSTEM

(75) Inventor: Gilles Mathieu, Lunel (FR)

(73) Assignee: FM-Assets PTY Ltd, Sydney (AU)

(*) Notice: Subject to any disclaimer, the term of this patent is extended or adjusted under 35 U.S.C. 154(b) by 771 days.

(21) Appl. No.: 12/450,488

(22) PCT Filed: Feb. 29, 2008

(86) PCT No.: PCT/IB2008/001304
§ 371 (c)(1),
(2), (4) Date: Sep. 28, 2009

(87) PCT Pub. No.: WO2008/122888
PCT Pub. Date: Oct. 16, 2008

(65) Prior Publication Data
US 2010/0110275 A1    May 6, 2010

(30) Foreign Application Priority Data
Apr. 6, 2007 (EP) .................... 07300936

(51) Int. Cl.
*G06K 9/00*    (2006.01)
(52) U.S. Cl.
USPC ............................................. 382/117; 348/77
(58) Field of Classification Search
USPC .................................................. 382/117, 298
See application file for complete search history.

(56) References Cited

U.S. PATENT DOCUMENTS

| | | | |
|---|---|---|---|
| 7,061,693 B2 | 6/2006 | Zalevski | |
| 7,095,901 B2 | 8/2006 | Lee et al. | |
| 7,158,317 B2 | 1/2007 | Ben-Eliezer et al. | |
| 7,209,293 B2 | 4/2007 | Gaida et al. | |
| 7,218,448 B1 | 5/2007 | Cathey et al. | |
| 7,224,540 B2 | 5/2007 | Olmstead et al. | |

(Continued)

FOREIGN PATENT DOCUMENTS

| | | |
|---|---|---|
| EP | 0730167 A2 | 2/1996 |
| JP | 2007678 | 11/1990 |

(Continued)

OTHER PUBLICATIONS

PCT International Search Report and Written Opinion for PCT/IB2008/001304 (Mailed Jun. 2, 2009).

(Continued)

*Primary Examiner* — John Strege
(74) *Attorney, Agent, or Firm* — Downs Rachlin Martin PLLC

(57) ABSTRACT

(A2) An extended depth of field (DOF) imaging system (10) is disclosed that has a corresponding extended depth of focus (DOF') by virtue of its optical system (20) having a select amount of spherical aberration. The imaging system has an image processing unit (54) adapted to process the raw images and perform contrast enhancement to form processed images. The image processing includes restoring the defocused modulation transfer functions (MTFs) using a gain function (G) and the amount of defocus. The imaging system can include an illumination system (60) that illuminates the object being imaged to establish a distance (DH) between the optical system and the object, where distance DH is used in the restoring of the MTF. An iris-recognition (I-R) system based on the enhanced DOF imaging system is also disclosed.; Optical system embodiments for use in the DOF imaging system that can provide select amounts of spherical aberration—and thus select increases in DOF—without increasing the adverse impact of other aberrations on image formation are also disclosed.

36 Claims, 19 Drawing Sheets

(56) References Cited

U.S. PATENT DOCUMENTS

| | | | |
|---|---|---|---|
| 7,365,917 | B2 | 4/2008 | Zalevski |
| 7,444,007 | B2 | 10/2008 | Schonberg |
| 7,593,550 | B2 | 9/2009 | Hamza |
| 2002/0131622 | A1 | 9/2002 | Lee et al. |
| 2004/0005083 | A1 | 1/2004 | Fujimura et al. |
| 2006/0050409 | A1 | 3/2006 | George et al. |
| 2006/0188274 | A1* | 8/2006 | Yasutomi .................. 399/27 |
| 2006/0198622 | A1* | 9/2006 | Xu et al. .................. 396/89 |
| 2007/0139541 | A1* | 6/2007 | Fein et al. .................. 348/294 |

FOREIGN PATENT DOCUMENTS

| | | |
|---|---|---|
| JP | 6162187 | 10/1994 |
| JP | 7084179 A | 3/1995 |
| JP | 08-069092 A | 3/1996 |
| JP | 2004226729 | 12/2004 |
| WO | WO9721188 | 6/1997 |
| WO | WO 99/57599 | 11/1999 |
| WO | WO 2006/083488 | 8/2006 |

OTHER PUBLICATIONS

Decision of Refusal for Japanese dated Jan. 24, 2012 for Japanese Counterpart Application JP 2010-501614 (original and translation).

Examination Report of Jun. 13, 2012 for EU counterpart Application 08 751 024.4.

* cited by examiner

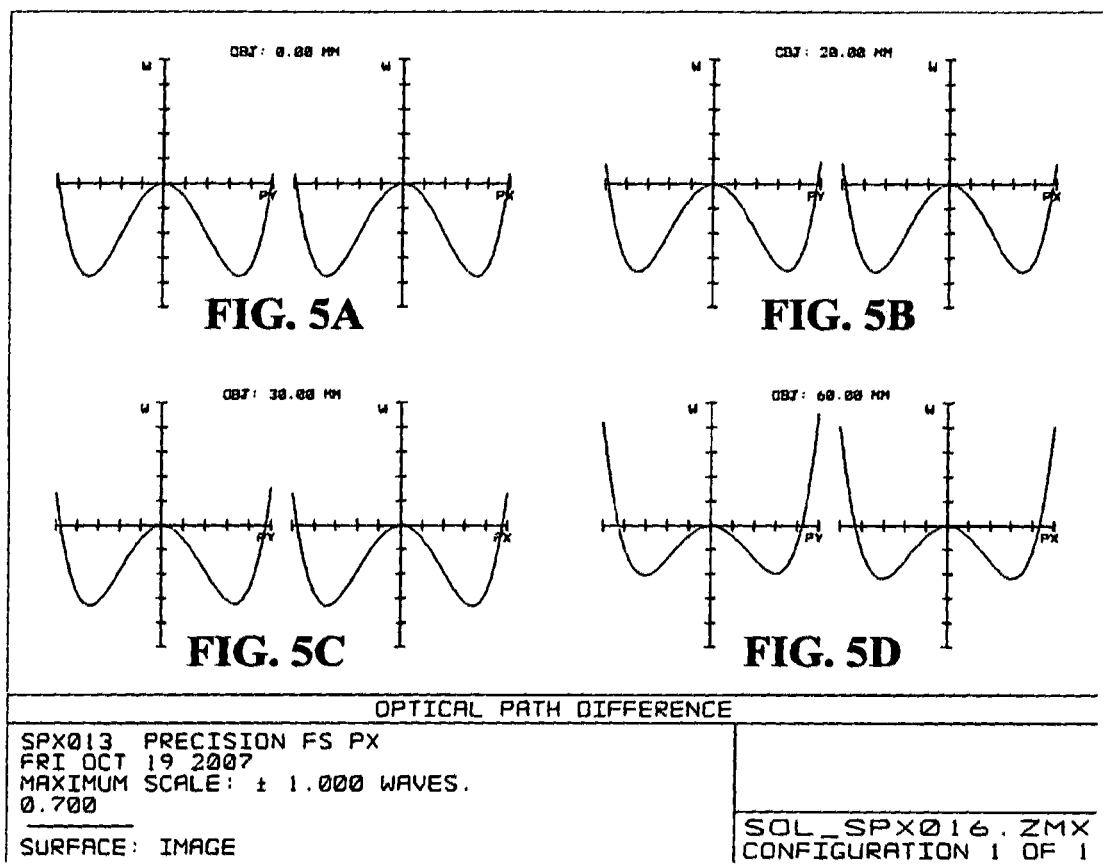

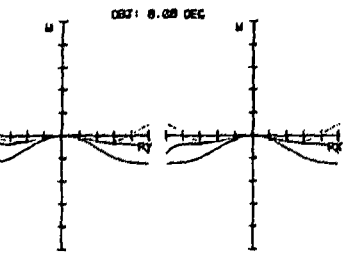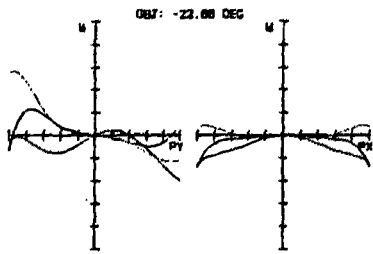
FIG. 7A    FIG. 7B
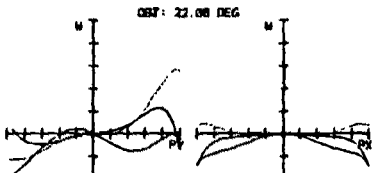
FIG. 7C
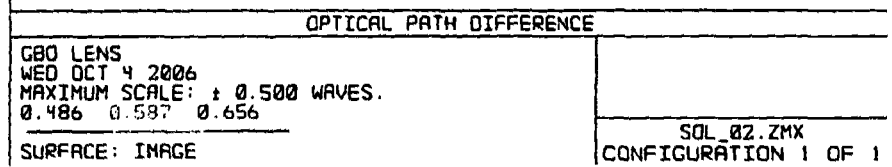
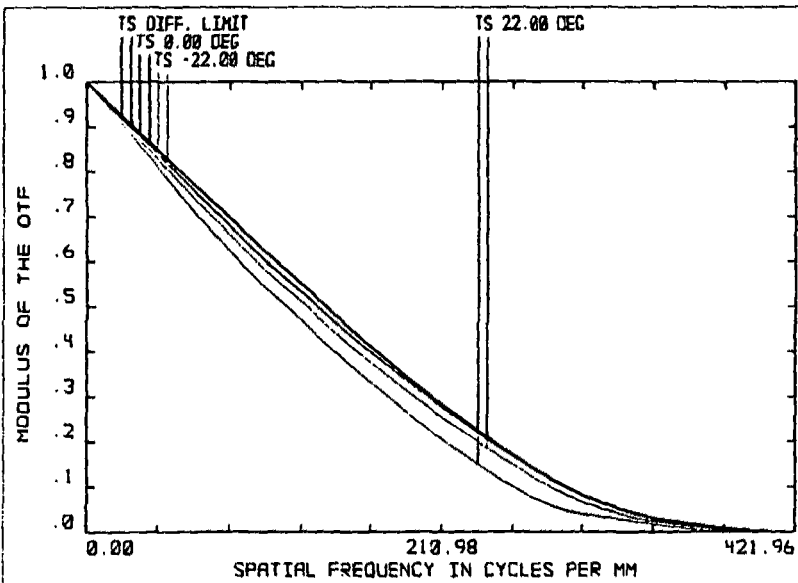
FIG. 7D
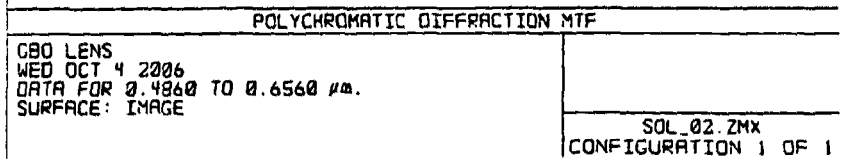

MTF'

LARGE DEPTH-OF-FIELD IMAGING SYSTEM AND IRIS RECOGNITON SYSTEM

CLAIM OF PRIORITY

This application claims the benefit of priority of European Patent Application No. EP 07300936.7, filed on Apr. 06, 2007, which patent application is incorporated by reference herein, and also claims the benefit of priority under 35 U.S.C. §365 of International Patent Application Serial No. PCT/IB2008/001304, filed on Feb. 29, 2008, designating the United States of America, which patent application is incorporated by reference herein.

BACKGROUND ART

1. Field of the Invention

The present invention relates generally to imaging systems, and particularly large depth-of-field imaging systems, and more particularly to large depth-of-field iris recognition systems.

2. Technical Background

Humans have a number of unique physical characteristics, such as fingerprints, iris patterns, and voices, whose measurement allows for distinguishing one person from another. The science of measuring such characteristics is known as "biometrics."

The measurement of a person's iris pattern to perform biometric identification ("authentication") is called "iris recognition." Iris recognition involves taking an image of a person's iris and then using pattern recognition techniques to create the equivalent of a "fingerprint" of the eye. Unlike fingerprints, however, iris images are obtained in a less obtrusive manner than fingerprints because they do not require physical contact with the subject.

Early work on iris recognition systems is described in the article by John G. Daugman, "How iris recognition works." IEEE transactions on Circuits and Systems for Video Technology, 14(1), January 2004, pp. 21-30, in U.S. Pat. No. 5,291,560 to Daugman, entitled "Biometric personal identification system based on iris analysis," and in U.S. Pat. No. 4,641,349 to Flom et al. entitled "Iris recognition system," which article and which patents are incorporated by reference herein.

Iris recognition requires that one or both irises be imaged with relatively high resolution so that as much iris detail as possible can be captured. The imaging must also be performed over a relatively large depth of field because the iris is three-dimensional and because some latitude is required in the exact position of the subject's eye relative to the optical system that captures the iris image. The optical system must also have a field-of-view (FOV) sufficient to capture not only the entire iris but also a portion of the face surrounding the eye to perform the necessary image processing.

A major shortcoming of many iris recognition systems is that the optical system requirements of large depth of field, sufficiently large FOV, and high-resolution are somewhat contradictory. For example, a high-resolution imaging system requires a relatively large numerical aperture (NA) (i.e., a low F/#), while a large depth of field requires a relatively low NA (or high F/#). A relatively high NA also decreases the light-gathering ability of the optical system so that longer exposure is required to capture an iris image. This, in turn, requires that the subject remain steady and that their eyes not move (or that they not blink) for a longer period of time so that the iris image is not blurred or obstructed.

A number of different approaches have been used to overcome the challenges posed by the optical design, including using wavefront coding and relatively complex optical systems. However, the need remains for an iris recognition system that has a simple yet robust optical system that provides the requisite optical imaging performance over a wide range of conditions and situations.

SUMMARY OF THE INVENTION

An aspect of the invention is an iris-recognition (I-R) system for capturing images of one or both irises of a person over a large depth of field (DOF). The I-R system includes an illumination system adapted to i) illuminate at an imaging wavelength $\lambda_{IM}$ a facial region of the person, wherein the facial region includes one or both eyes and at least a forehead portion of the person, and ii) to form a spot on the forehead portion. The I-R system also includes an optical system having an object plane within the large depth of field DOF, an image plane within a correspondingly large depth of focus DOF'. An image sensor is arranged at the image plane. The optical system is provided with an amount of spherical aberration (SA) at an imaging wavelength $\lambda_{IM}$ such that the depth of field DOF increases by an amount between 50% and 500% as compared to the optical system being diffraction limited. The optical system is configured to form on the image sensor an image of the facial region when the facial region is placed within the depth of field DOF. The facial region image includes an image of the forehead spot. The I-R system also includes a controller electrically connected to the image sensor and to the illumination system. The controller is adapted to control and coordinate the operation of the illumination system and the image sensor. It is also adapted to perform image processing on the facial-region image to form an enhanced image of one or both irises based on an enhanced modulation transfer function (MTF) formed using the forehead distance information obtained from the forehead spot.

Another aspect of the invention is a method of forming an enhanced image of at least one iris of a person. The method includes forming a raw image of a facial region of the person that includes at least one eye of the person and a forehead portion of the person. The raw image is formed using an optical system having an amount of spherical aberration that increases the DOF of the optical system by an amount between 50% and 500% as compared to the optical system being diffraction limited. The method also includes using an image sensor to electronically capture the raw image to form a digitized raw image, with the raw image having a corresponding raw modulation transfer function (MTF). The method then includes establishing an amount of defocus in the digitized raw image based on a position of the person relative to the optical system. The method also includes forming an enhanced MTF from the raw MTF by multiplying the raw MTF by a gain function that depends on the amount of defocus. The method further includes applying the enhanced MTF to the digitized raw image to obtain the enhanced image.

Another aspect of the invention is an enhanced DOF imaging system for forming an enhanced-contrast image of an object. The system includes an optical system having an amount of spherical aberration (SA) at an imaging wavelength $\lambda_{IM}$ such that the DOF increases by an amount between 50% and 500% as compared to the optical system being diffraction limited. The optical system is configured to form an image of the object at an image plane when the object is within the DOF and at a distance away from the optical system. The imaging system also includes an image sensor located at the image plane and adapted to form an electrical signal representative of the image as a raw image. The imaging system also includes a controller electrically connected to the image sensor and having image processing capability, wherein the controller is adapted to receive the electrical signal and perform image-processing on the raw image to form an enhanced image using an enhanced modulation transfer function (MTF) formed based on said object distance.

It is to be understood that both the foregoing general description and the following detailed description present embodiments of the invention, and are intended to provide an overview or framework for understanding the nature and character of the invention as it is claimed. The accompanying drawings are included to provide a further understanding of the invention, and are incorporated into and constitute a part of this specification. The drawings illustrate various embodiments of the invention, and together with the description serve to explain the principles and operations of the invention.

BRIEF DESCRIPTION OF THE DRAWINGS

FIG. 5A-5D are plots of the optical path difference (OPD) for various image heights for an optical system having $0.7\lambda$ of spherical aberration;

FIGS. 7A-7C are OPD plots for red, blue and green wavelength light for the optical system set forth in Table 2A and shown in FIG. 6B;

FIG. 7D is a plot of the modulation transfer function (MTF) for the optical system set forth in Table 3A and shown in FIG. 6B;

DETAILED DESCRIPTION

Figure 1:
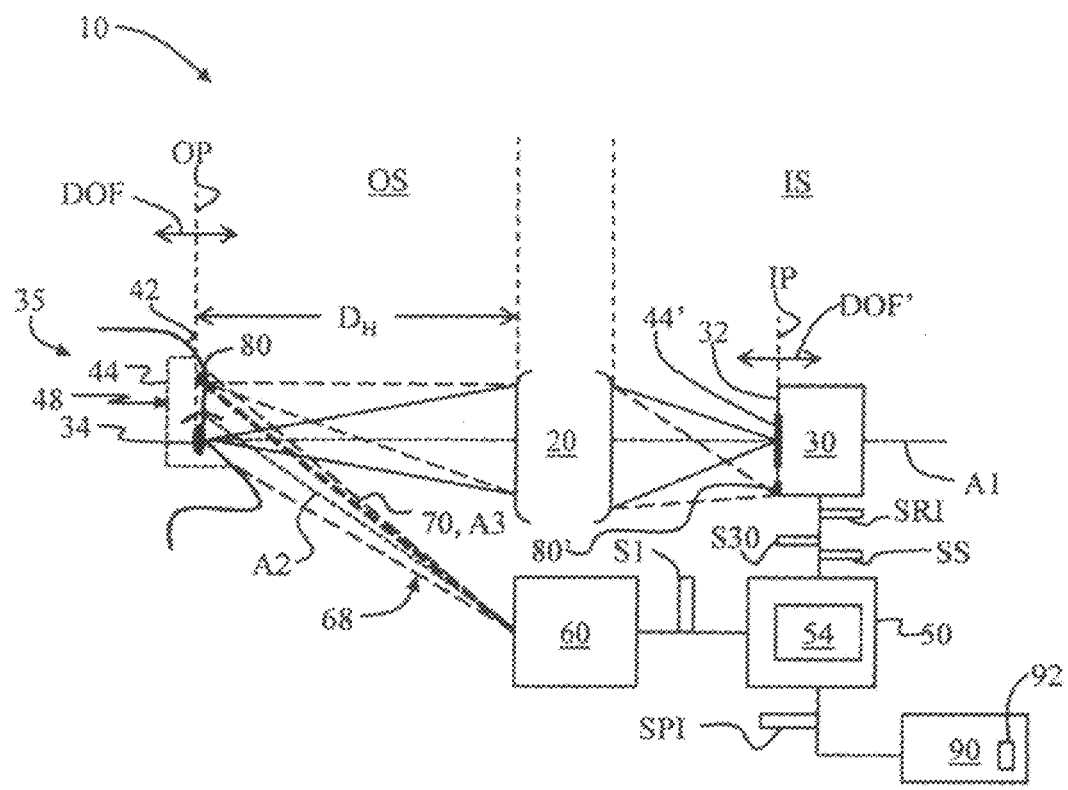
FIG. 1 is a schematic diagram of a generalized embodiment of an iris-recognition (I-R) system according to the present invention.

Reference is now made in detail to the present preferred embodiments of the invention, examples of which are illustrated in the accompanying drawings. Whenever possible, like or similar reference numerals are used throughout the drawings to refer to like or similar parts. Various modifications and alterations may be made to the following examples within the scope of the present invention, and aspects of the different examples may be mixed in different ways to achieve yet further examples. Accordingly, the true scope of the invention is to be understood from the entirety of the present disclosure, in view of but not limited to the embodiments described herein.

The present invention is directed to enhanced DOF imaging systems. A generalized iris-recognition system based on the enhanced DOF imaging system of the present invention is first discussed, followed by more detailed descriptions of the various components that make up the I-R system, along with the corresponding methods and processes that make up the invention.

Generalized Iris-Recognition System

FIG. 1 is a schematic diagram of a generalized embodiment of an iris-recognition ("I-R") system 10 according to the present invention. I-R system 10 includes an optical axis A1 along which is arranged an imaging optical system 20 that has a lateral magnification $M_L$, an axial magnification $M_A=(M_L)^2$, an object plane OP in an object space OS and an image plane IP in an image space IS. Optical system 20 has a depth of field DOF in object space OS over which the object can be imaged and remain in focus. Likewise, optical system 20 has a corresponding depth of focus DOF' in image space IS over which an image of an object remains in focus. Object and image planes OS and IS are thus idealizations of the positions of an object and the corresponding image and typically correspond to an optimum object position and a "best focus" position, respectively. In actuality, these planes can actually fall anywhere within their respective depth of field DOF and depth of focus DOF'. The depth of field DOF and depth of focus DOF' are defined by the properties of optical system 20 and their interrelationship and importance in the I-R system of the present invention is discussed more fully below.

I-R system 10 also includes an image sensor 30 that has a photosensitive surface 32 (e.g., an array of charge-coupled devices) arranged at image plane IP of the optical system so as to be in optical communication with optical system 20.

Figure 2:
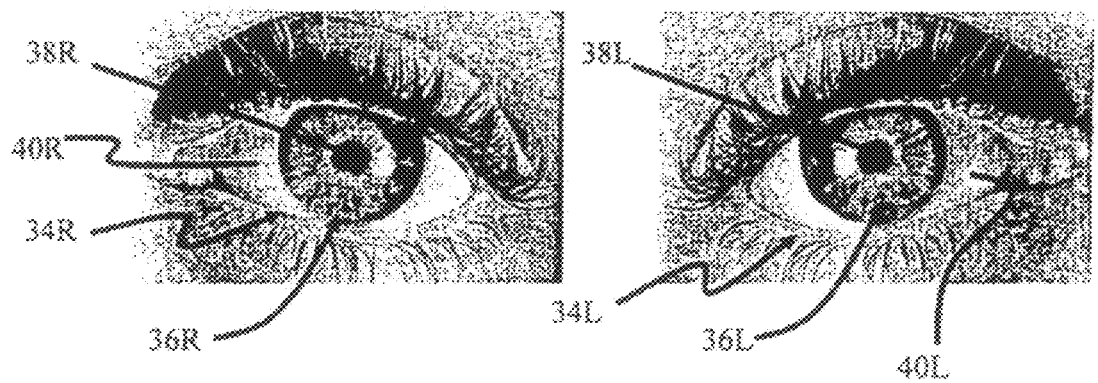
FIG. 2 is a close-up image of the eyes of person showing the left and right irises, the left and right pupils, and the left and right sclera, wherein "left" and "right" here are taken relative to the person.

A person 35 is located in object space OS and a portion of their face ("face portion" 44) that includes their eyes 34 serves as the "object" for optical system 20. FIG. 2 is a close-up image of eyes 34L and 34R of person 35 showing the left and right irises 36L and 36R, the left and right pupils 38L and 38R, and the left and right scleras 40L and 40R. Note that "left" and "right" here are taken relative to person 35.

Person 35 is situated such that their left and right eyes 34L and 34R are located within the depth of field DOF (e.g., at object plane OP) of optical system 20. The person's forehead 42 is located a distance $D_H$ from optical system 20. Distance $D_H$ is referred to herein as the "forehead distance" and is used to establish the proper placement of eyes 34 relative to optical system 20, as discussed below. Optical system 20 is configured to form an image 44' of face portion 44, wherein the face-portion image 44' includes images of eyes 34L and 34R, and in particular the irises 36L and 36R thereof. Image 44' also includes the person's forehead or a portion thereof for reasons discussed below.

I-R system 10 further includes a controller 50, such as a computer or like machine, that is adapted (e.g., via instructions such as software embodied in a computer-readable or machine-readable medium) to control the operation of the various components of the I-R system. Examples of controller 50 are discussed below.

Controller 50 includes an image-processing unit 54. Image-processing unit 54 is electrically coupled to image sensor 30 and is adapted to receive and process raw image signals SRI from the image sensor and form therefrom processed image signals SPI.

I-R system 10 also includes an illumination system 60 electronically coupled to controller unit 50. Illumination system 60 is configured to provide a first illumination beam 68 along an optical axis A2 that illuminates face portion 44 with a corresponding illumination region 48. Illumination system is also configured to provide a second illumination beam 70 along an axis A3 that forms a mark such as a spot 80 on the person's forehead 42. Illumination system 60 is controlled by controller 50 via an illuminator control signal S1.

I-R system 10 also includes a database unit 90 operably connected to controller 50. Database unit 90 includes a memory unit 92 that serves as a computer-readable medium adapted to receive processed image signals SPI and store the processed digital images of irises 36L and 36R as represented by the processed image signals. Memory unit ("memory") 92 may be any computer-readable medium, including but not limited to RAM, ROM, EPROM, PROM, EEPROM, disk, floppy disk, hard disk, CD-ROM, DVD, or the like, on which data may be stored. In an example embodiment, database unit 90 is included in controller 50. Database unit 90 thus contains a library of iris images that can be used to compare against other iris images to perform personnel authentication.

In the general operation of I-R system 10, person 35 is first properly positioned in object space OP so that their eyes 34 are within the depth of field DOF of optical system 20. Controller 50 then sends an illuminator control signal S1 to illumination system 60, which causes the illumination system to generate illumination beam 68. Illumination beam illuminates face region 44 with illumination region 48. Controller 50 also sends a control signal S30 to activate image sensor 30 for a given exposure time so that face-portion image 44' formed optical system 20 is captured by photosensitive surface 32. Image sensor 30 digitizes the "raw" image 44' and creates the electronic raw image signal SRI representative of the raw captured image. Image signal SRI is provided to controller 50 and in particular to image processing unit 54 therein. In an example embodiment, image sensor 30 forms a separate electronic spot signal SS from the portion of image 44' that includes spot 80 so that the spot signal can be processed separately from image signal SI.

Image processing unit 54 then digitally processes the raw image signal SRI to form a corresponding processed image embodied in electronic processed image signal SPI. Image processing unit 54 also extracts from raw image signal SRI the spot signal SS (or uses a spot signal SS sent from image sensor 30) to establish distance $D_H$ via triangulation, as discussed below. Image processing unit 54 uses distance $D_H$ to digitally process (e.g., filter, compress, etc.) raw image signals SRI to form the aforementioned processed image signals SPI that digitally represent enhanced images of irises 36L and 36R. These images can then be used separately or used together to perform iris recognition.

Controller 50 is then used to access the stored processed iris images in database unit 90 and compare them to other stored iris images or to recently obtained processed iris images to perform personnel identification.

Optical System

As discussed above, imaging optical system 20 has a depth of field DOF in object space OS and a depth of focus DOF' in image space IS as defined by the particular design of the optical system. The depth of field DOF and the depth of focus DOF' for conventional optical imaging systems can be ascertained by measuring the evolution of the Point Spread Function (PSF) through focus, and can be established by specifying an amount of loss in resolution R that is deemed acceptable for a given application. The "circle of least confusion" is often taken as the parameter that defines the limit of the depth of focus DOF'.

In the present invention, both the depth of field DOF and the depth of focus DOF' are extended by providing optical system 20 with an amount of spherical aberration (SA). In an example embodiment, $0.2\lambda_{IM} \leq SA \leq 5\lambda_{IM}$, where $\lambda_{IM}$ is the imaging wavelength. In an example embodiment, the amount of spherical aberration in the optical system at the imaging wavelength $\lambda_{IM}$ is such that the depth of field DOF or the depth of focus DOF' increases by an amount between 50% and 500% as compared to the optical system being diffraction limited. By adding select amounts of spherical aberration, the amount of increase in the depth of field DOF can be controlled. The example optical system designs set forth below are configured to be able to add select amounts of spherical aberration—and thus select increases in depth of field DOF—without increasing the adverse impact of other aberrations on image formation.

Since the depth of field DOF and the depth of focus DOF' are related by the axial magnification $M_A$ and lateral magnification $M_L$ of optical system 20 via the relationships DOF'= $(M_A)$ DOF= $(M_L)^2$ DOF, I-R system 10 is said to have an "extended depth of field" for the sake of convenience. One skilled in the art will recognize that this expression also implies the I-R system has an "extended depth of focus" as well. Thus, either the depth of field DOF or the depth of focus DOF' is used below, depending on the context of the discussion.

The Modulation Transfer Function (MTF) can also be used in conjunction with the PSF to characterize the depth of focus DOF' by examining the resolution R and contrast C of the image through focus. Here, the "modulation" or "contrast" $C=(I_{MAX}-I_{MIN})/(I_{MAX}+I_{MIN})$ is measured for an image of a set of sinusoidal line-space pairs having a particular spatial frequency, where $I_{MAX}$ and $I_{MIN}$ are the maximum and minimum image intensities, respectively. The best focus is defined as the image position where the MTF is maximized and where the PSF is the narrowest. When an optical system is free from aberrations (i.e., is diffraction limited), the best focus based on the MTF coincides with the best focus based on the PSF. However, when aberrations are present in an optical system, the best focus positions based on the MTF and PSF can differ.

Conventional lens design principles call for designing an optical system in a manner that seeks to eliminate all aberrations, or to at least balance them to minimize their effect so that the optical system on the whole is substantially free of aberrations.

Figure 3A:
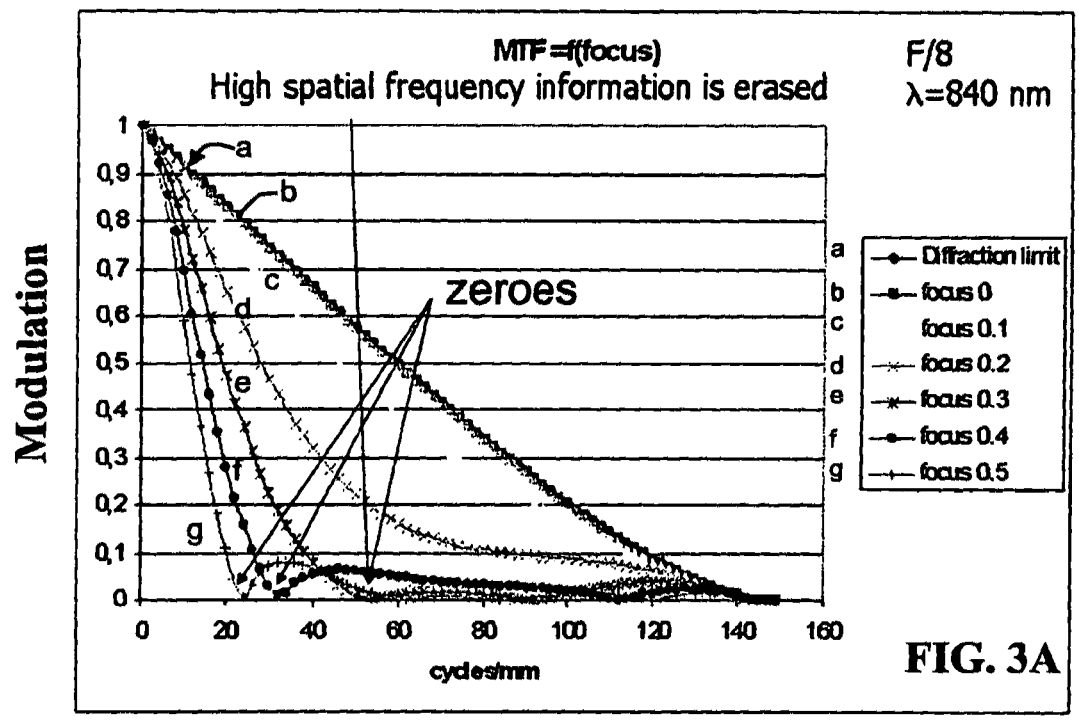
FIG. 3A is a plot of the diffraction-limited modulation transfer function (MTF) for varying amounts of defocus indicated by curves a through g.
Figure 3B:
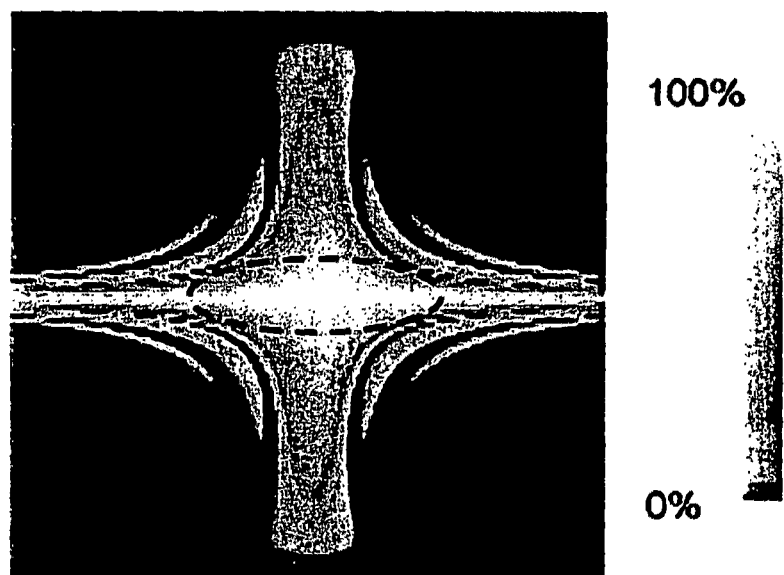
FIG. 3B is a plot of the light intensity distribution through focus for an idealized imaging optical system, with the dashed ellipse indicating the depth of focus.
Figure 4A:
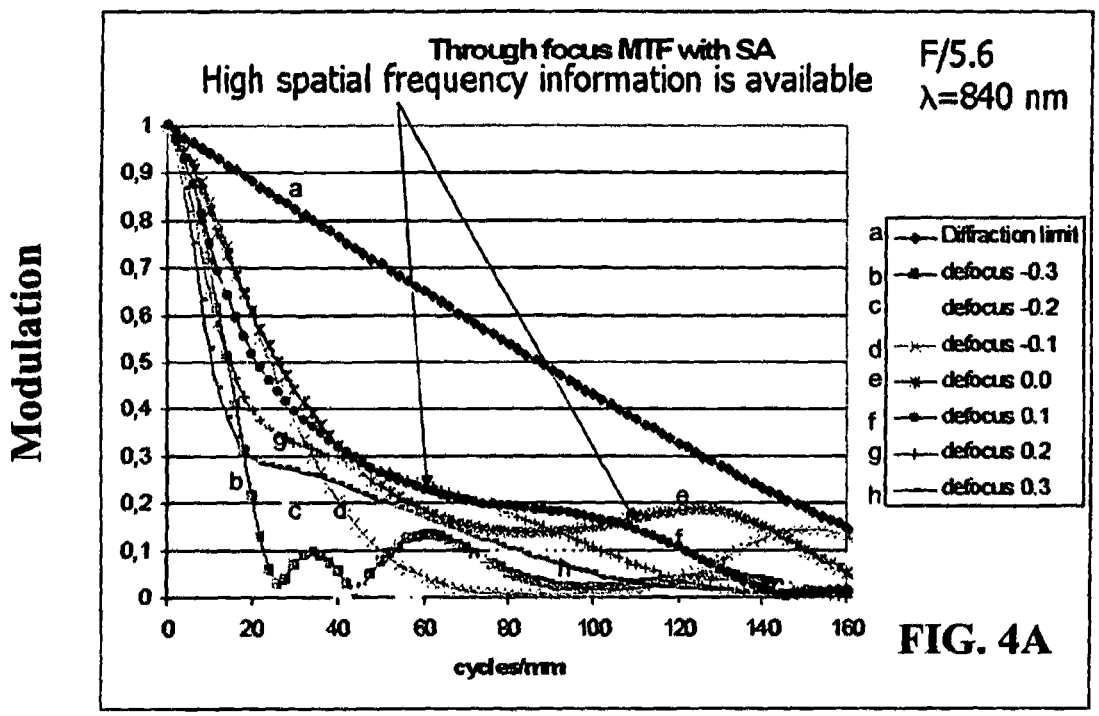
FIG. 4A is a plot of the modulation transfer function (MTF) for varying amounts of defocus for the imaging optical system having $0.75\lambda$ of spherical aberration, along with the zero-focus diffraction limited MTF for comparison, as indicated by curves a through h.
Figure 4B:
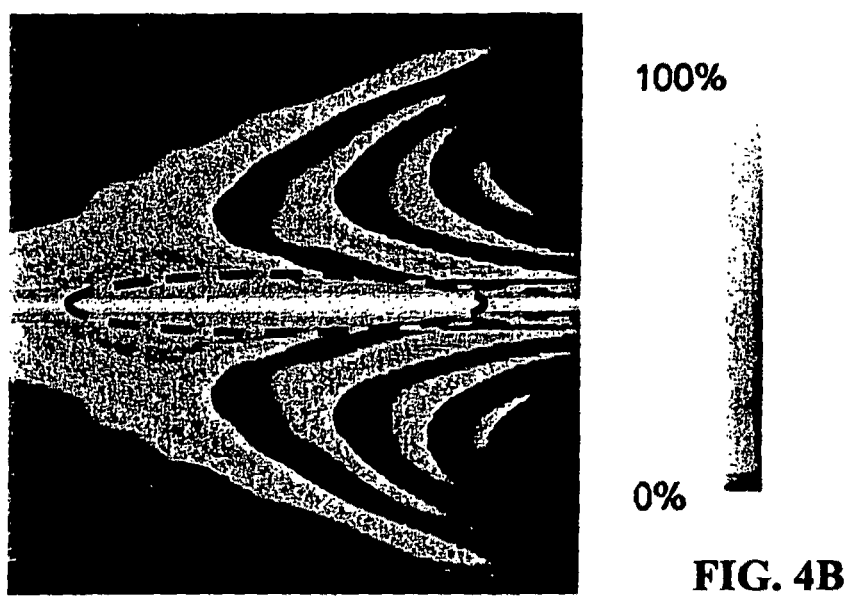
FIG. 4B is the same type of light intensity plot as FIG. 4A, but for the MTF for FIG. 4A, illustrating how the depth of focus (dashed line) is extended as compared to the diffraction-limited case of FIG. 3B by virtue of the presence of spherical aberration.

However, in the present invention, optical system 20 is intentionally designed to have spherical aberration as a dominant aberration, and optionally has a small amount of chromatic aberration as well. FIG. 3A is a plot of the MTF for an F/8 lens without aberrations (curves a through g), while FIG. 4A is a plot of an MTF for an F 5.6 lens that has 0.75 waves of spherical aberration (curves a through h). FIG. 3B is an intensity plot through focus for the diffraction-limited case of the F/8 lens of FIG. 3A, and FIG. 4B is an intensity plot through focus for the F/5.6 lens with spherical aberration of the lens of FIG. 4A. FIGS. 5A-5D are plots of the optical path difference (OPD) for various image heights (0 mm, 20 mm, 30 mm and 60 mm, respectively) for an optical system having $0.7\lambda$ of spherical aberration.

The spherical aberration reduces the contrast of the image by reducing the overall level of the MTF from the base frequency $f_0=0$ to the cutoff frequency $f_C$. The cut off frequency $f_C$ is not significantly reduced as compared to the ideal (i.e., diffraction-limited) MTF, so nearly all the original spatial-frequency spectrum is available. Thus, the spatial-frequency information is still available in the image, albeit with a lower contrast. The reduced contrast is then restored by digital filtering carried out by image processing unit 54, as described below. The spherical aberration increases the depth of focus DOF' in the sense that the high spatial frequencies stay available over a greater range of defocus. The digital filtering restores the contrast and good quality image over the enhanced depth of focus DOF' thereby effectively enhancing the imaging performance of optical system 20.

Spherical aberration is an "even" aberration in the sense that the wavefront error $W(\rho)=\rho^4$, wherein $\rho$ is the pupil coordinate. Thus, the spherical aberration presents a rotationally symmetric wave front error so that the phase is zero. This means that the resulting Optical Transfer Function (OTF) (which is the Fourier Transform of the PSF) is a rotationally symmetric, real function. The MTF, which is the magnitude of the OTF, can be obtained where spherical aberration is the dominant aberration by considering a one-dimensional MTF measurement taken on a slanted edge. This measurement provides all the required information to restore the two-dimensional image via digital signal processing. Also, the phase is zero at any defocus position, which allows for digital image processing to enhance the MTF without the need to consider the phase component (i.e., the phase transfer function, or PFT) of the OTF in the Fourier (i.e., spatial-frequency) space.

As can be seen from FIG. 4A, because the image-wise side of the defocus (as measured from the "best focus" plane) has no zero in the MTF when there is spherical aberration present, there is no contrast inversion. This allows for an image to be formed and detected in this extended depth of focus DOF' (see dashed ellipse in FIG. 4B) to be restored without having to account for detrimental ringing, overshoot or other image artifacts.

Figure 4C:
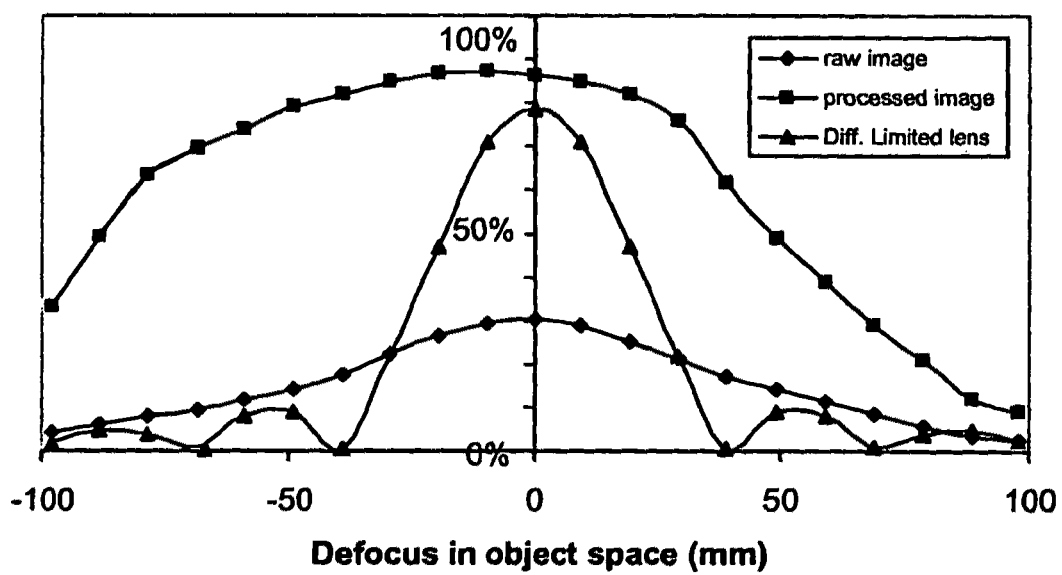
FIG. 4C plots the through-focus MTF at 3 line-pairs per millimeter (lp/mm) in object space for NA=0.0063.

In an example embodiment, optical system 20 is provided with an amount of spherical aberration SA wherein $0.2\lambda \leq SA \leq 5\lambda$, and more preferably $0.2\lambda \leq SA \leq 0.9\lambda$, and even more preferably $0.2\lambda \leq SA \leq 0.75\lambda$. An amount of spherical aberration of $SA=0.75\lambda$, gives a significant DOF enhancement without forming a zero in the MTF on one defocus side. Beyond $0.75\lambda$, a zero occurs on both sides of defocus from the best focus. For a diffraction-limited optical system, the depth of focus DOF' is given by the relationship $DOF'=\pm\lambda/(NA^2)$, where NA is the numerical aperture of the optical system. In an example embodiment, optical system 20 has an NA between about 0.0625 and 0.125 (i.e., F/8 to F/4 where F/#=NA/2 and operates at a center wavelength of $\lambda$=800 nm and a bandwidth of $\Delta\lambda$, which provides a diffraction-limited depth of focus DOF' of 20 mm. The introduction of $0.75\lambda$ of spherical aberration increases the depth of focus DOF' to 100 mm, which is an increase of about five times over the diffraction-limited depth of field DOF. FIG. 4C plots the through-focus MTF at 3 lp/mm in object space.

Single-Lens Example Optical System

Figure 6A:
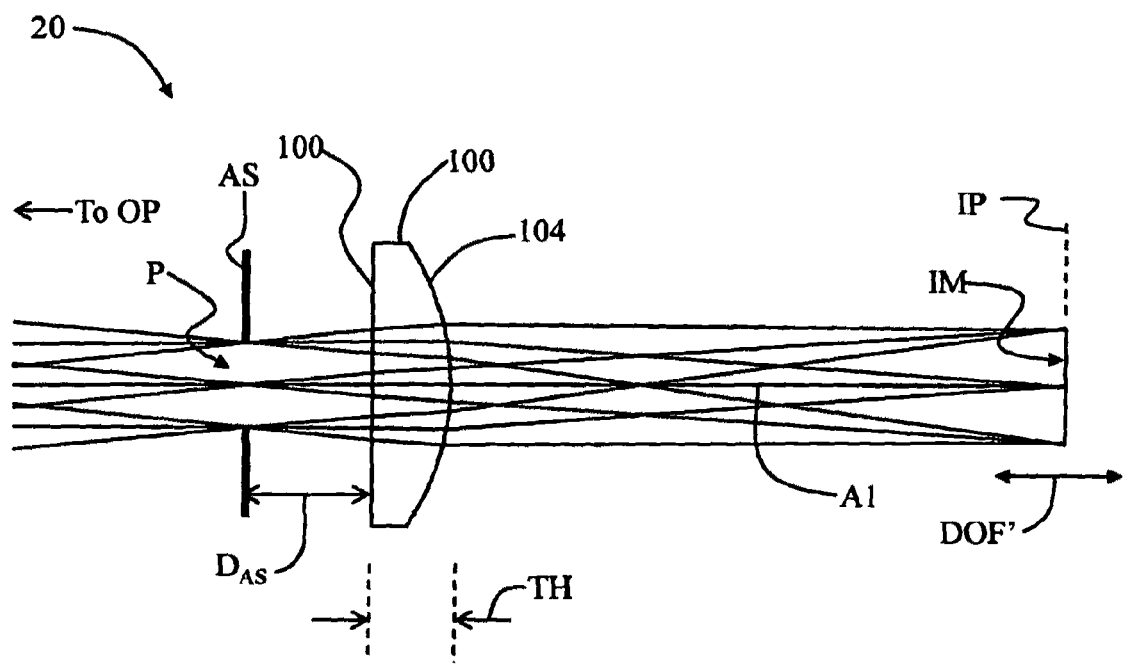
FIG. 6A is a schematic diagram of an example embodiment of the optical system of the I-R system of FIG. 1, wherein the optical system includes a single lens element that provides an enhanced depth of field.

FIG. 6A is a schematic side view of a first example embodiment of optical system 20 according to the present invention. Optical system 20 includes a single lens element 100 arranged along optical axis A1. Lens element 100 has a front (i.e., object-wise) surface 102 and a rear (i.e., image-wise) surface 104, and a center (axial) thickness TH. An aperture stop AS is arranged along optical axis A1 a distance $D_{AS}$ away from lens front surface 102 and defines a pupil P having a radial coordinate $\rho$. Pupil P also defines the optical systems entrance and exit pupils as viewed from the object and image spaces, respectively. In an example embodiment, lens element 100 is a plano-convex lens with surface 102 being the plano surface. Also in an example embodiment, surface 104 is an aspheric surface. Lens element 100 forms an image IM at image plane IP.

Table 1 below sets forth an example design for optical system 20 based on single lens 100.

TABLE 1

Example optical system for the I-R system

| | |
|---|---|
| Lens Type | Single Plano-Convex |
| Material | Fused Silica |
| | $n_d = 1.458464$ |
| | $v_d = 67.82$ |
| Radius of curvature of image-wise curved surface 104 | 23 mm |
| Center (axial) thickness TH | 7 mm |
| Working diameter | 14 mm |
| Entrance pupil diameter | 8 mm |
| $D_{AS}$ | 11 mm |
| F/# | 6.6 |
| Center wavelength λ | =800 nm (near IR) |
| Wavelength bandwidth Δλ | 40 nm to 200 nm |
| Focal length | 50 mm |
| Working Depth of Focus DOF' | 0.77 mm ~5X (or 500%) greater than the diffraction limited DOF'. |
| Lateral Magnification $M_L$ | (1/11.4) |
| Clear Aperture CA | 12 mm |
| Depth of Field DOF | =100 mm |
| Resolution R | =3 lines/mm |
| Spherical aberration | 0.75 λ |
| Chromatic aberration | 0.4 mm in [735 nm-890 nm] |
| Coma | Null |
| Field Curvature | Radius in image space: −20 mm |
| Astigmatism | <λ/10 |

This simple, single-element design for lens 100 provides the required spherical aberration at F/6.6 that matches well to the required practical working conditions for performing iris recognition. Other options for lens 100 include plastic as the material, an F/# in the range from F/4 to F/8. An advantage of a single-element design for optical system 20 is that it makes the system very compact so that the overall I-R system 10 can be made compact.

Distance $D_E$ of aperture stop AS and pupil P is that at which minimizes comatic aberration. The astigmatism of lens 100 is about λ/10 and so does not significantly affect the image quality. A single-element design is not entirely corrected for chromatic aberration, which can be advantageous in that some chromatic aberration can be used to further increase the depth of field DOF when used with a relatively large imaging bandwidth $\Delta\lambda_{IM}$ by eliminating some zeroes in the MTF that might otherwise occur. Otherwise, the chromatic aberration is limited by using an Abbe number V>60 so as not to diminish the MTF by introducing lateral color in the edge of the field of a relatively large field. The axial chromatic aberration can be set at different values by the choice of glass. Standard optical glass has an Abbe number in the range from 20 to 64.

Though axial chromatic aberration increases the depth of field DOF, the MTF level decreases. This in turn requires increasing the MTF amplification in the digital processing, which increases the SNPD (Spectral Noise Power Density). The Abbe number is thus preferably selected to achieve a good compromise between diminishing the MTF while increasing the depth of field DOF. In an example embodiment, the glass material is selected such the added increase in the depth of field DOF (i.e., added to the increase provided by the spherical aberration) is up to 20%, while the decrease in the average MTF level is no more than about 25%.

Fused Silica (Abbe number of 67.8) is good glass choice when using an imaging wavelength $\lambda_{IM}$ having a relatively wide near-IR spectral bandwidth, e.g., $\Delta\lambda_{IM}$=155 nm (e.g., from 735 nm to 890 nm). In an example embodiment, an acceptable amount of axial chromatic aberration is about 0.34 mm in the image space. When using a narrow-band imaging spectrum $\Delta\lambda_{IM}$ such as from a single LED array with a near-IR spectral bandwidth $\Delta\lambda_{IM}$ of about 50 nm FWHM, the axial chromatic aberration is smaller so that more dispersive glasses can be used. In lens 100 of Table 1, the chromatic aberration is 10 μm at the field edge.

Field curvature needs to take into account to set the best focus plane. The lens 100 as set forth in Table 1 has a field curvature of 60 mm in object space or −20 mm in image space. However, since field curvature is simply a form of defocus, adverse effects presented by this amount of field curvature can be overcome by the gain in depth of focus DOF' due to the presence of spherical aberration.

Lens 100 of Table 1 has a resolution of R=120 μm in object space, which is more than adequate to resolve details in the pattern of iris 36 in order to perform iris recognition.

Double-Gauss-Type Example Optical System

Figure 6B:
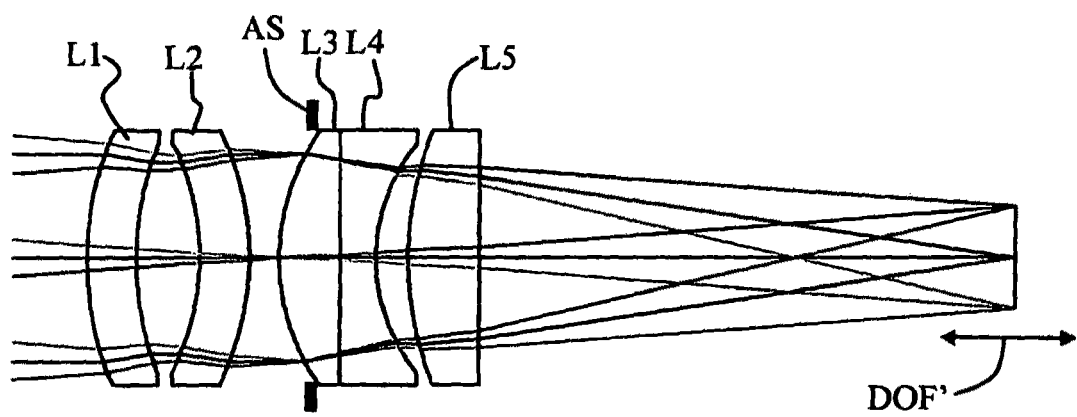
FIG. 6B is a schematic diagram of an example embodiment of an optical system of the I-R system of FIG. 1, wherein the optical system included multiple elements based on a double-Gauss layout.

FIG. 6B is a schematic side view of a second example embodiment of optical system 20 according to the present invention. Optical system 20 of FIG. 3B is based on a double-Gauss design and includes five lens elements labeled L1 through L5 objectwise to imagewise. Lenses L1 and L2 are opposing meniscus lenses with the convex surface of lens L1 being on the object side while the convex surface of lens L2 is on the image side. Lens L1 is weakly positive, while lens L2 is weakly negative. In one embodiment, the combination of lenses L1 and L2 form a front lens group having overall weak negative power, while in another example embodiment this front lens group has no optical power, i.e., is afocal.

Lenses L4 and L5 are respectively a plano-convex positive lens and a plano-concave negative lens that are contacted at their flat surfaces to form a doublet. Lens L5 is a plano-convex lens with its convex surface on the object side.

Tables 2A and 2B below set forth an example lens design prescription for the optical system 20 of FIG. 6B that has minimal spherical aberration (Table 2A) and a relatively large amount of spherical aberration of 0.75 waves (Table 2B) intentionally introduced into the lens by adjusting the surface curvatures of lens L2.

In Table 2A and Table 2B, as well as in the other Tables below, "S#" is the surface number, "SRF" is the surface description, "C" is the curvature in mm, "R" is the radius in mm, "TH" is the thickness in mm, "Glass" is the glass type, and "D" is the diameter in mm.

TABLE 2A

Lens Design Prescription for optical system 20 of FIG. 6B without spherical aberration

| S# | SRF | C | R | TH | Glass | D |
|---|---|---|---|---|---|---|
| 1 | | 0.00E+00 | | | | 22.45 |
| 2 | L1 | 4.07E−02 | 24.55 | 4.00 | N-LAF34 | 20.00 |
| 3 | | 4.19E−02 | 23.87 | 5.20 | | 18.00 |
| 4 | L2 | −5.21E−02 | −19.9 | 4.00 | N-PSK53 | 18.00 |
| 5 | | −4.55E−02 | −22 | 2.50 | | 20.00 |
| 6 | L3 | 5.95E−02 | 16.8 | 4.90 | N-SK14 | 20.00 |
| 7 | L4 | 0.00E+00 | | 3.00 | N-SF15 | 20.00 |
| 8 | | 7.16E−02 | 13.96 | 2.60 | | 18.00 |
| 9 | L5 | 4.00E−02 | 25 | 5.98 | N-BASF64 | 20.00 |
| 10 | | 0.00E+00 | | 43.63 | | 20.00 |
| 11 | image | 0.00E+00 | | 0.00 | | 8.08 |

TABLE 2B

Lens Design Prescription for optical system 20 of
FIG. 6B with 0.75 waves of spherical aberration

| S# | SRF | C | R | TH | Glass | D |
|---|---|---|---|---|---|---|
| 1 | | 0.00E+00 | | | | 22.45 |
| 2 | L1 | 4.07E−02 | 24.55 | 4.00 | N-LAF34 | 20.00 |
| 3 | | 4.19E−02 | 23.87 | 5.20 | | 18.00 |
| 4 | L2 | −4.65E−02 | −21.5 | 4.00 | N-PSK53 | 18.00 |
| 5 | | −4.07E−02 | −24.55 | 2.50 | | 20.00 |
| 6 | L3 | 5.95E−02 | 16.8 | 4.90 | N-SK14 | 20.00 |
| 7 | L4 | 0.00E+00 | | 3.00 | N-SF15 | 20.00 |
| 8 | | 7.16E−02 | 13.96 | 2.60 | | 18.00 |
| 9 | L5 | 4.00E−02 | 25 | 5.98 | N-BASF64 | 20.00 |
| 10 | | 0.00E+00 | | 43.63 | | 20.00 |
| 11 | image | 0.00E+00 | | 0.00 | | 8.08 |

The optical design set forth in Table 2B includes 0.75 waves of spherical aberration that arises from adjusting the surface curvatures of just one lens, namely lens L2 (see underlined values). This example illustrates how a "conventional" optical design can be modified to have a spherical aberration that increases the depth of focus DOF' for the system. In the present example embodiment, the depth of focus DOF' increase is about a factor of 4× over the diffraction-limited version of the same lens.

Negative-Positive Lens Example Embodiment

Figure 6C:
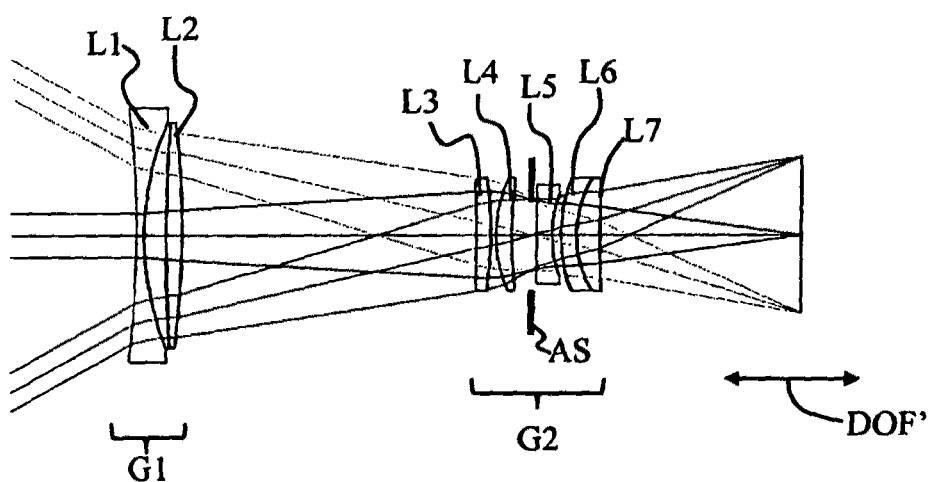
FIG. 6C is a schematic diagram of an example embodiment of an optical system of the I-R system of FIG. 1, wherein the optical system employs a two-element front negative lens group and a five-element rear positive lens group.

FIG. 6C is a schematic side view of a second example embodiment of optical system 20 according to the present invention. Optical system 20 includes a first negative lens group G1 that includes two lens elements L1 and L2, and a second positive lens group that contains three lens elements L3, L4, L5, L6 and L7. Aperture stop AS is located between lens elements L4 and L5 and is immediately adjacent element L5.

Table 3A sets forth an example lens design prescription for optical system 20 of FIG. 6C that has minimal spherical aberration, while Table 3B sets forth an example lens design prescription for optical system 20 of FIG. 6C that 0.75 waves of spherical aberration intentionally introduced into the design.

TABLE 3A

Lens Design Prescription for optical system 20 of
FIG. 6B without spherical aberration

| S# | SRF | C | R | TH | Glass | D |
|---|---|---|---|---|---|---|
| 1 | | 0.00E+00 | | | | 27.10 |
| 2 | L1 | −2.04E−02 | −49.07 | 0.74 | SK10 | 18.00 |
| 3 | | 6.13E−02 | 16.31 | 2.00 | | 16.00 |
| 4 | L2 | 1.21E−02 | 82.52 | 1.50 | SK15 | 16.00 |
| 5 | | −1.89E−02 | −53.02 | 28.00 | | 16.00 |
| 6 | L3 | 0.00E+00 | | 1.50 | BASF2 | 8.00 |
| 7 | | −4.94E−02 | −20.23 | 0.50 | | 8.00 |
| 8 | L4 | 1.34E−01 | 7.48 | 1.50 | FK3 | 8.00 |
| 9 | | 4.74E−02 | 21.09 | 1.80 | | 7.00 |
| 10 | | 0.00E+00 | | 0.60 | | 5.00 |
| 11 | L5 | 0.00E+00 | | 1.50 | SF15 | 7.00 |
| 12 | | 1.55E−01 | 6.43 | 0.90 | | 6.00 |
| 13 | L6 | 1.16E−01 | 8.64 | 1.50 | SF5 | 8.00 |
| 14 | L7 | 1.64E−01 | 6.10 | 2.25 | LAKN12 | 8.00 |
| 15 | | 1.41E−02 | 70.95 | 19.16 | | 8.00 |
| 16 | | 0.00E+00 | | 0.00 | | 11.10 |

TABLE 3B

Lens Design Prescription for optical system 20 of
FIG. 6B with 0.75 waves of spherical aberration

| S# | SRF | C | R | TH | Glass | D |
|---|---|---|---|---|---|---|
| 1 | | 0.00E+00 | | | | 27.10 |
| 2 | L1 | −2.04E−02 | −49.07 | 0.74 | SK10 | 18.00 |
| 3 | | 6.13E−02 | 16.31 | 2.00 | | 16.00 |
| 4 | L2 | 1.21E−02 | 82.52 | 1.50 | SK15 | 16.00 |
| 5 | | −1.89E−02 | −53.02 | 28.00 | | 16.00 |
| 6 | L3 | 0.00E+00 | | 1.50 | BASF2 | 8.00 |
| 7 | | −4.94E−02 | −18.83 | 0.50 | | 8.00 |
| 8 | L4 | 1.34E−01 | 6.78 | 1.50 | FK3 | 8.00 |
| 9 | | 4.74E−02 | 12.87 | 1.80 | | 7.00 |
| 10 | | 0.00E+00 | | 0.60 | | 5.00 |
| 11 | L5 | 0.00E+00 | | 1.50 | SF15 | 7.00 |
| 12 | | 1.55E−01 | 6.53 | 0.90 | | 6.00 |
| 13 | L6 | 1.16E−01 | 8.64 | 1.50 | SF5 | 8.00 |
| 14 | L7 | 1.64E−01 | 6.10 | 2.25 | LAKN12 | 8.00 |
| 15 | | 1.41E−02 | 70.95 | 19.16 | | 8.00 |
| 16 | | 0.00E+00 | | 0.00 | | 11.10 |

The 0.75 waves of spherical aberration of the design as set forth in Table 3B arises from lenses L3, L4 and L5 (see underlined values in Tables 3A and 3B).

FIGS. 7A, 7B and 7C are optical path difference (OPD) plots (sagittal and tangential planes) for blue, green and red imaging wavelengths $\lambda_{IM}$ (486 nm, 587 nm and 656 nm, respectively) for the "no spherical aberration" lens design set forth in Table 3A. The optical path difference plots show some residual aberrations, mainly secondary chromatic aberrations and coma. However, these aberrations are relatively small, as demonstrated in the MTF plot for the lens as shown in FIG. 7D, which shows the MTF as being close to the diffraction-limited MTF.

Figure 8A:
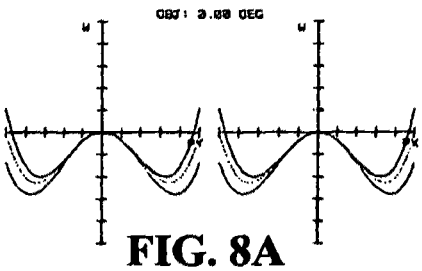
FIG. 8A-8C are OPD plots for red, blue and green wavelength light for the optical system set forth in Table 3B and shown in FIG. 6C.
Figure 8B:
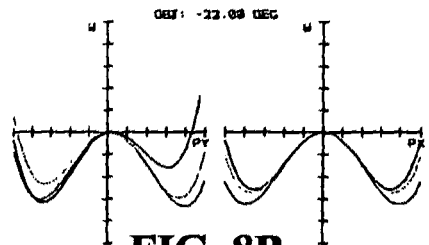
Figure 8C:
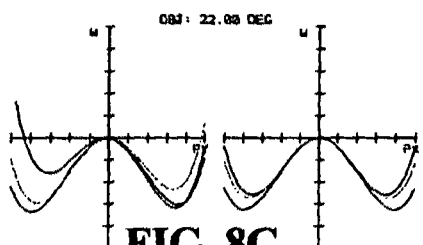
Figure 8D:
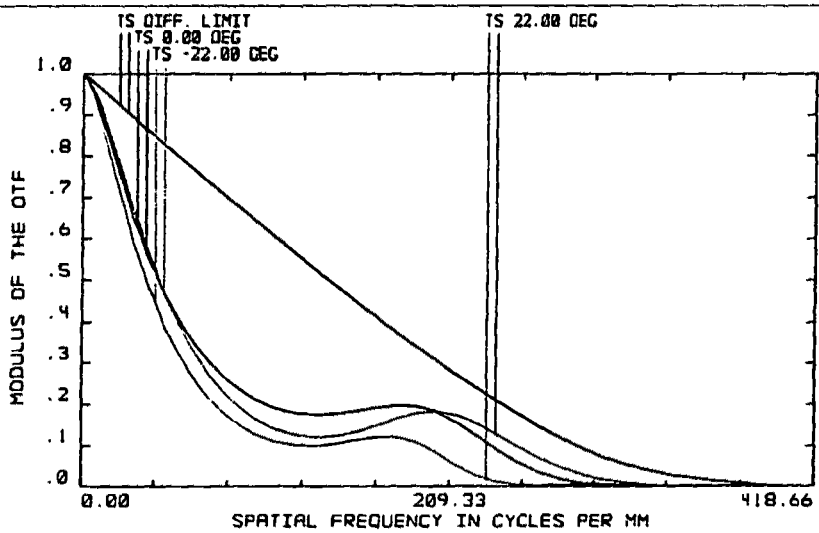
FIG. 8D is a plot of the modulation transfer function (MTF) for the optical system set forth in Table 3 and shown in FIG. 6C.

FIGS. 8A, 8B and 8C are OPD plots similar to those of FIGS. 7A, 7B and 7C but for the "spherical aberration" lens design set forth in Table 3B. FIG. 8D is a plot of the MTF of the lens design set forth in Table 3B.

Illumination System and Forehead Distance Measurement

Figure 9:
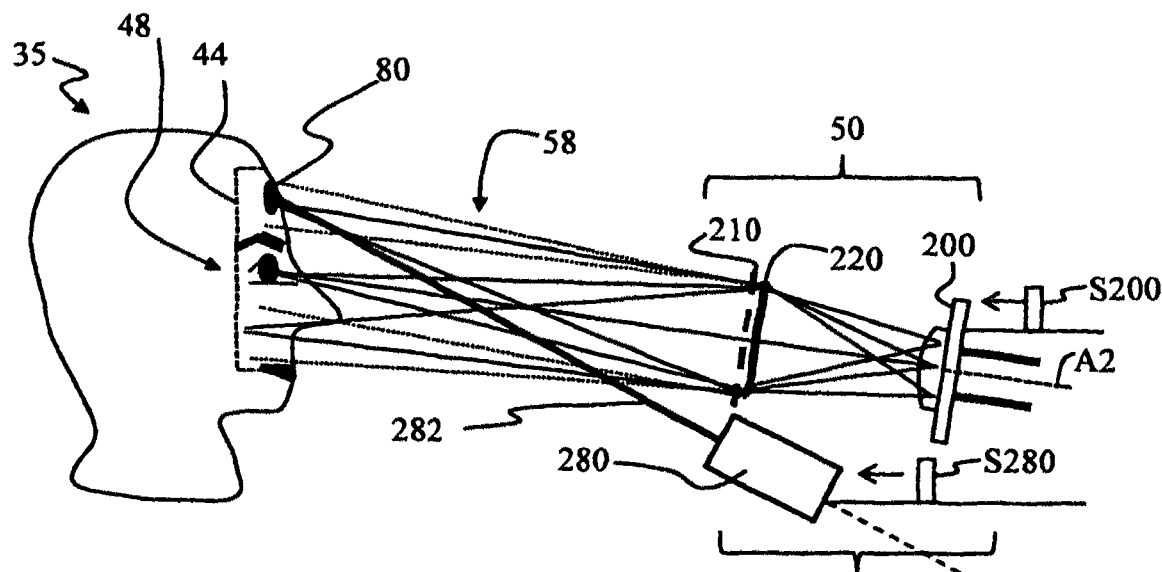
FIG. 9 is a schematic diagram of an example embodiment of the illumination system of the I-R system of FIG. 1.

As discussed above, I-R system 10 includes an illumination system 60 configured to illuminate face region 44 with a corresponding illumination region 48, and to form on forehead 42 a spot 80 used measure forehead distance $D_H$. FIG. 9 is a schematic diagram of an example embodiment of illumination system 60 that includes a light source 200, a diffuser 210 and a collimating lens 220 all arranged in order along optical axis A2. In an example embodiment, light source 200 includes a light-emitting diode (LED) array that emits light centered on illumination wavelength $\lambda_I$ with a wavelength band $\Delta\lambda_I$. An example LED array size is 8 mm×8 mm.

In an example embodiment, $\Delta\lambda_I$~200 nm, e.g., between 700 nm and 900 nm. A preferred illumination wavelength is $\lambda_I$=810 nm, which makes illumination beam 68 less visible and thus less disturbing for person 35. An illumination wavelength of $\lambda_I$=810 nm is also particularly good for imaging blue and brown eyes. Also, high-resolution image sensors 30 are available that are sensitive over an illumination wavelength band $\Delta\lambda_I$ of 700 nm and 900 nm. The relatively large illumination bandwidth also mitigates speckle effects. Another reason to use near-IR wavelengths for the illumination wavelength $\lambda_I$ is that such wavelengths do not cause pupil dilation.

In an example embodiment, collimating lens 220 is a Fresnel lens that operates at F/1 and that has a focal length of 50 mm. In another example embodiment, diffuser 210 is a holographic diffuser configured to have a homogeneous angular distribution of about 3°.

In operation, the LED array of light source 200 is imaged by collimating lens 220 onto face region 44 that includes the eyes 34 of person 35 to form an illumination region 48 thereon. However, illumination region 240 is smoothed by the action of diffuser 210 so that the face-region image 44' formed by optical system 20 at image sensor 30 has sufficiently high quality for image processing.

In an example embodiment, illumination system 50 provides an average irradiance in illumination region 48 of about 10 mW/cm$^2$, which provides an exposure time to capture face-region image 44' of about 20 ms. In an example embodiment, the LED array current is a 20 ms constant pulse of 5A. This allows a good signal-to-noise (S/N) ratio at a 20 ms exposure time at F/6.6 in face region 44.

In an example embodiment, face region 44 and collimating lens 220 are separated by a distance $D_F$ in the range from about 500 mm to about 700 mm, and the size of face illumination region 48 is about 120 mm×120 mm. Also, the average angle of incidence $\theta_2$ of illumination beam 68 as measured between optical axis A2 and optical axis A1 is about 7°, as illustrated in the simplified schematic diagram of I-R system 10 of FIG. 10. Illumination region 48 is formed such that it does not disturb face region image 44' by avoiding the creation of detrimental imaging effects such as the so-called "red eye" effect produced by light backscattering from the eye's retina. The uniformity of illumination in illumination region 48 also avoids dangerous irradiance peaks that could be imaged on the retina. The irradiance level of illumination region 48 is that which is safe for eyes 34, and in an example embodiment is about 10 mW/cm$^2$.

Light source 200 is triggered by signal S200 from controller 50. In an example embodiment, signal S200 is triggered in response to a general-purpose output (GPO) signal $S_{GPO}$ from image sensor 30 to controller 50 that sets the synchronization between the facial illumination from illumination system 60 and the exposure time of the image sensor in capturing face image 44' via optical system 20.

Illumination system 50 also includes an infrared (IR) or near-IR laser source 280 arranged along an optical axis A3 and that generates a substantially collimated laser beam 282 that forms aforementioned spot 80 on forehead 42. In an example embodiment, optical axis A3 is tilted relative to optical axes A1 and A2 and is arranged so that laser beam 282 shines upward toward the person's forehead 42 from below rather than downward onto the forehead from above.

Figure 10A:
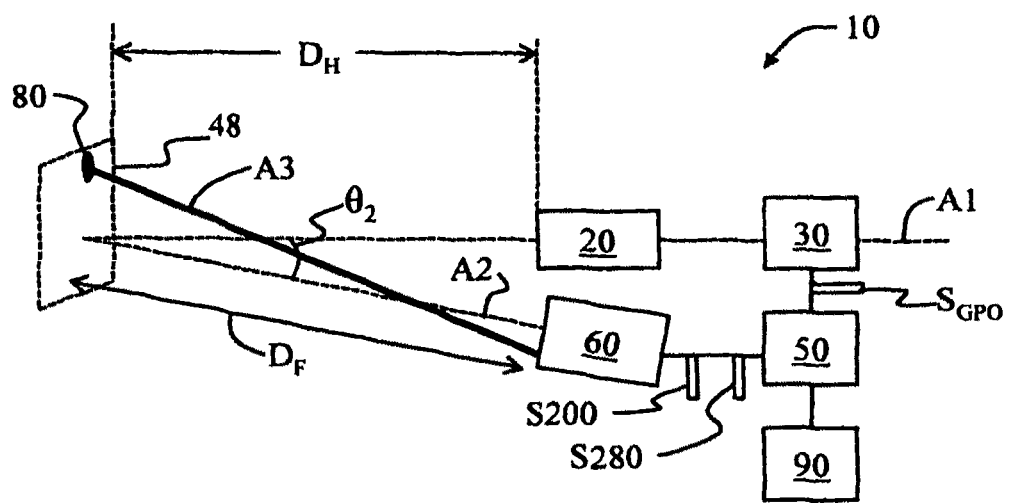
FIG. 10A, FIG. 10B and FIG. 11 are schematic diagrams of the I-R system similar to that shown in FIG. 1, showing the illumination region and a number of key geometric parameters used to measure forehead distance $D_H$.
Figure 10B:
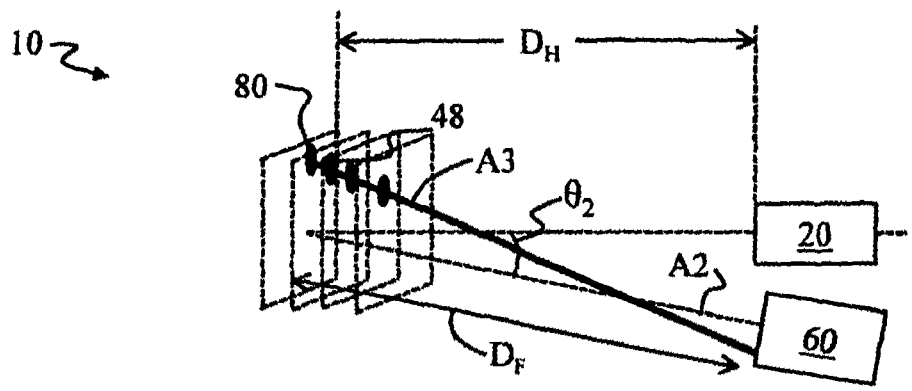
Figure 11:
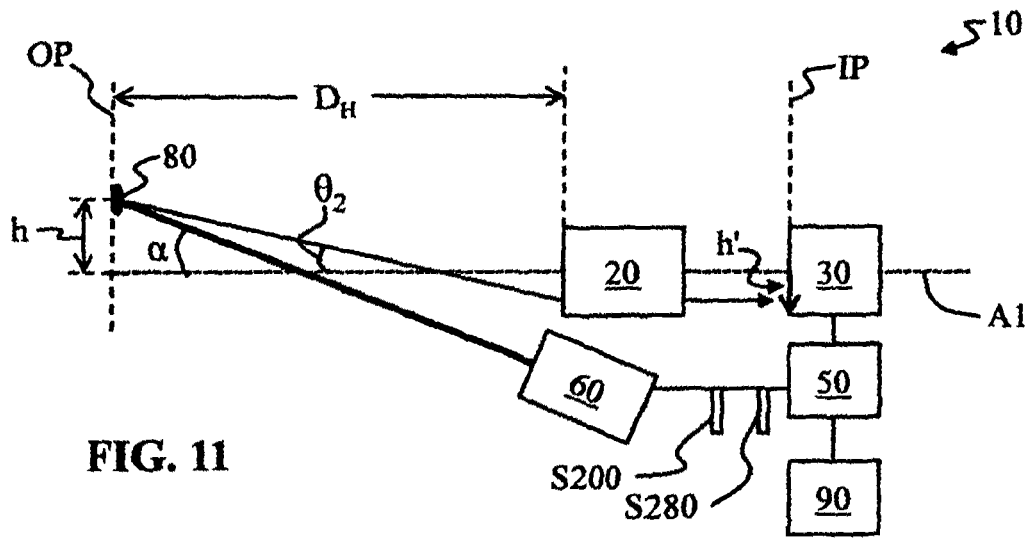

FIG. 11 is a schematic diagram similar to FIG. 10 that illustrates the main geometrical parameters for calculating distance $D_H$ using laser source 200. Because laser beam 282 (and this optical axis A3) forms an angle $\alpha$ with respect to optical axis A1, the height h of spot 80 changes as the image-wise distance from laser source 280 increases. The change in height h can be carefully measured as a function of distance $D_H$. Furthermore, height h can be measured by measuring its image height h' as formed by optical system 20 at image sensor 30. Spot height h and its image height h' are related by h=$(M_L)$ h', where $M_L$ is the aforementioned lateral magnification of optical system 20. Thus, measuring the image height h' at image sensor 30, and knowing the optical system's lateral magnification $M_L$ provides the spot image height h'.

Figure 12:
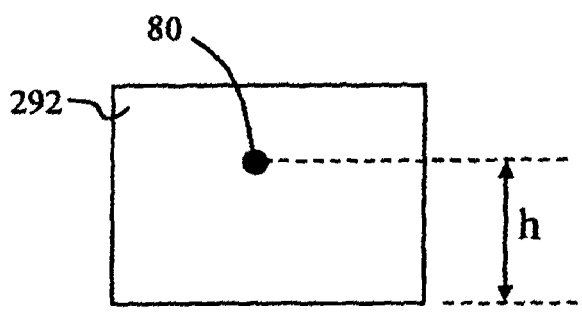
FIG. 12 is a front on view of a screen used to calibrate the distance measurement for forehead distance $D_H$ has a function of spot height h.
Figure 13:
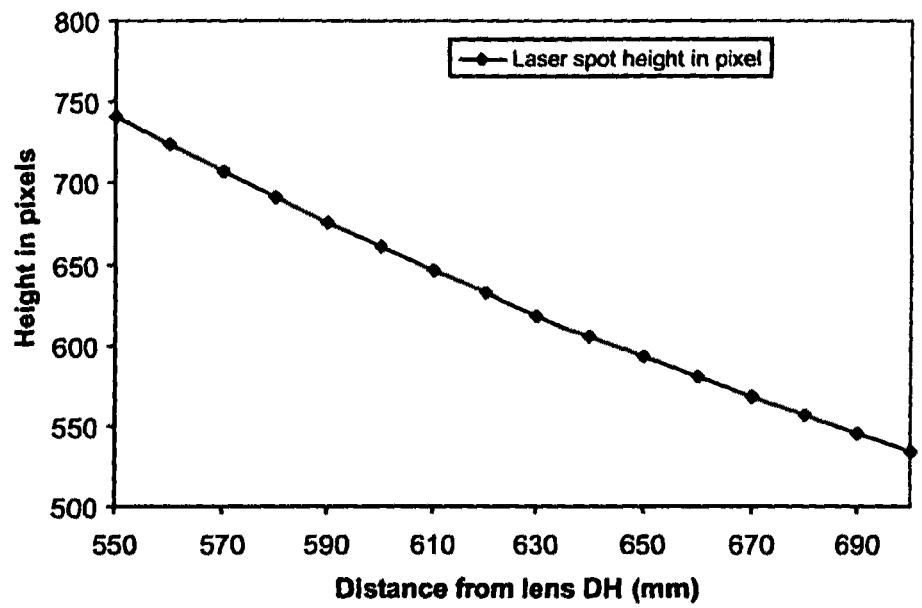
FIG. 13 is a plot of the laser spot image height h' as a function of forehead distance $D_H$.

With reference now to FIG. 12, in an example embodiment, a white screen 292 is used to establish spot heights h (and thus corresponding image heights h') for spot 80 for various axial distances $D_H$. This process is used to establish the distance $D_H$ to an accuracy of about 1 mm, or for a typical distance $D_H$=600 mm, about 0.2%. The results of this calibration exercise are shown in FIG. 13, which plots the image height h' (in pixels) versus (head) distance $D_H$. This establishes the relationship between h, h' and the forehead distance $D_H$ via triangulation. In an example embodiment, this calibration is stored in controller 50 as a data table or look-up table, and accessed (e.g., by image processor 54) during the operation of I-R system 10. Linear interpolation is used to establish distances $D_H$ that fall between measured values for height h.

Image Sensor

In an example embodiment, image sensor 30 is or otherwise includes a high-definition CCD camera or CMOS camera. In a preferred embodiment, photosensitive surface 32 is made up of 3000×2208 pixels, with a pixel size of 3.5 microns. The full-well capacity is reduced to 21,000 electrons for a CMOS camera at this small pixel size, which translates into a minimum of shot noise of 43.2 dB at saturation level.

An example image sensor 30 is or includes a camera from Pixelink PL-A781 3000×2208 pixels linked by IEEE1394 Fire Wire to controller 50, and the application calls API provided by a Pixelink library in a DLL to control the camera and make acquisition of images. In an example embodiment, image sensor 30 is adapted to provide the aforementioned GPO $S_{GPO}$ that is used to synchronize the activation of illumination system 60 to illuminate face region 44 with the image capture by image sensor 30 of face region image 44'.

Controller

Figure 14:
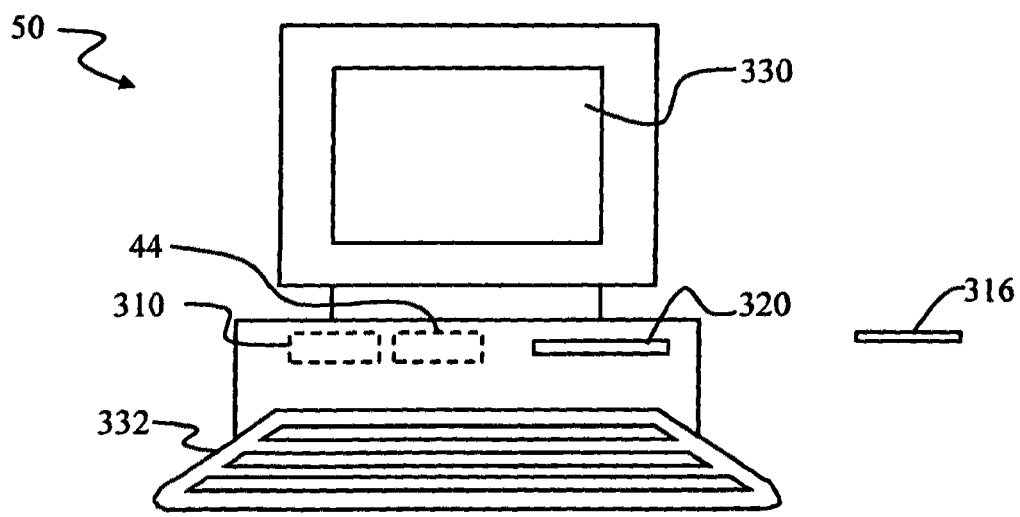
FIG. 14 is a schematic diagram of an example embodiment of a controller of the I-R system of FIG. 1.

As discussed above, controller 50 is configured to control the operation of I-R system 10 and includes image processing unit 54 adapted to receive and process raw digital images from image sensor 30. An example controller is schematically illustrated in FIG. 14. In an example embodiment, controller 50 is or includes a computer with a processor and includes an operating system such as Microsoft WINDOWS or LINUX.

In an example embodiment, image processor 54 is or includes any processor or device capable of executing a series of software instructions and includes, without limitation, a general- or special-purpose microprocessor, finite state machine, controller, computer, central-processing unit (CPU), field-programmable gate array (FPGA), or digital signal processor. In an example embodiment, the processor is an Intel XEON or PENTIUM processor, or an AMD TURION or other in the line of such processors made by AMD Corp., Intel Corp. or other semiconductor processor manufacturer.

Controller 10 also preferably includes a memory unit ("memory") 310 operably coupled to image processor 50. As used herein, the term "memory" refers to any processor-readable medium, including but not limited to RAM, ROM, EPROM, PROM, EEPROM, disk, floppy disk, hard disk, CD-ROM, DVD, or the like, on which may be stored a series of instructions executable by image processor 54. In an example embodiment, controller 50 includes a disk drive 320 adapted to accommodate a removable processor-readable medium 316, such as CD-ROM, DVE, memory stick or like storage medium.

The iris-recognition methods of the present invention, including operating I-R system 10, may be implemented in various embodiments in a machine-readable medium (e.g., memory 310) comprising machine readable instructions (e.g., computer programs and/or software modules) for causing controller 50 to perform the methods and the controlling operations for operating the I-R system. In an example embodiment, the computer programs run on image processor 54 out of memory 310, and may be transferred to main memory from permanent storage via disk drive 320 when stored on removable media 316, or via a network connection or modem connection when stored outside of controller 50, or via other types of computer or machine-readable media from which it can be read and utilized.

The computer programs and/or software modules may comprise multiple modules or objects to perform the various methods of the present invention, and control the operation and function of the various components in I-R system 10. The type of computer programming languages used for the code may vary between procedural code type languages to object oriented languages. The files or objects need not have a one to one correspondence to the modules or method steps described depending on the desires of the programmer. Further, the method and apparatus may comprise combinations of software, hardware and firmware. Firmware can be downloaded into image processor 54 for implementing the various example embodiments of the invention.

Controller 50 also optionally includes a display 330 that can be used to display information using a wide variety of alphanumeric and graphical representations. For example, display 330 is useful for displaying processed iris images, and for reporting on authentication results based on compared iris images. Controller 50 also optionally includes a data-entry device 332 such as a keyboard that allows a user of I-R system 10 to input information into controller 50 (e.g., the name of the person being measured by the I-R system), and to manually control the operation of the I-R system.

Image Processing

Image processor 54 is adapted to receive from image sensor 30 electrical signals SRI containing raw face-region images 44' and process the raw images to form processed images that have higher contrast. This is accomplished by filtering the raw images in a manner that restores the MTF as a smooth function that decreases continuously with spatial frequency f and that preferably avoids overshoots, ringing and other image artifacts.

Noise amplification is often a problem in any filtering process that seeks to sharpen a signal (e.g., enhance contrast in a digital optical image). Accordingly, an optimized gain function (similar to Wiener's filter) that takes in account the power spectrum of noise is applied in the present invention to reduce noise amplification during the contrast-enhancing process.

The gain function applied to the "raw" MTF to form the "enhanced" MTF depends on distance $D_H$. The MTF versus distance $D_H$ is acquired by a calibration process wherein the MTF is measured in the expected depth of field range by using a sampling defocus steps $\delta_F \leq (1/8)(\lambda/(NA^2))$ to avoid any undersampling and thus the loss of through-focus information for the MTF.

Figure 15:
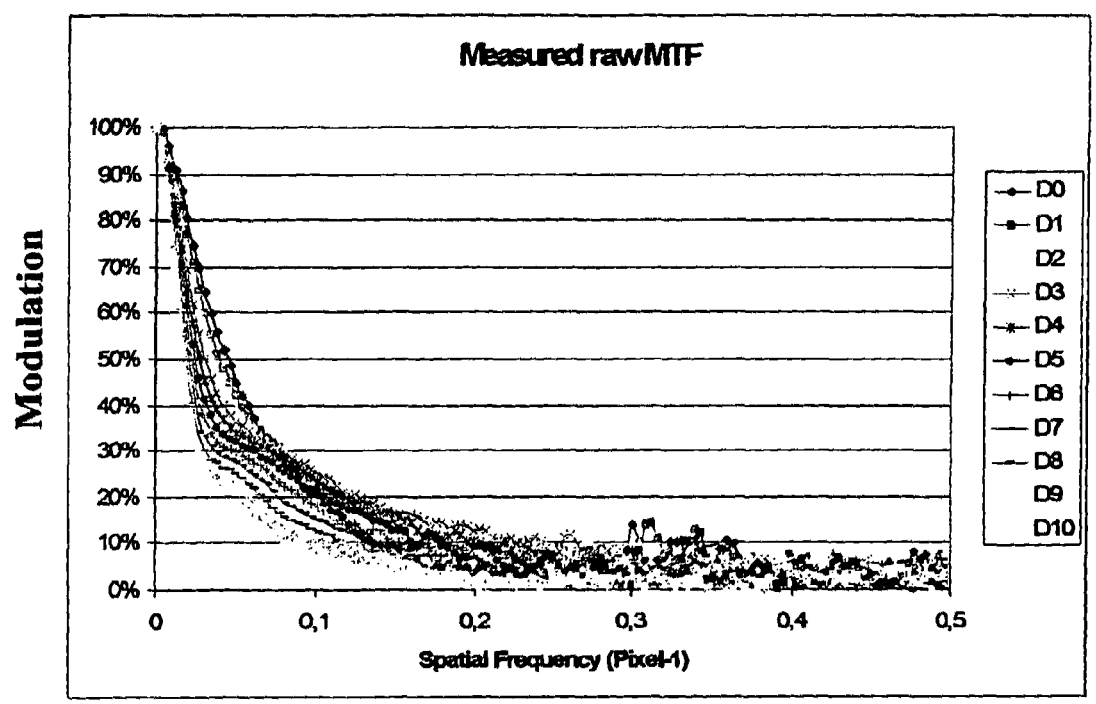
FIG. 15 is a plot of the measured (raw) MTF for various defocus positions for the optical system of the I-R system of FIG. 1.

FIG. 15 plots the measured or "raw" MTFs as measured at different defocus distances $\delta_F$ of 10 mm from best focus between extremes of −50 mm and +50 mm of defocus. For each step through defocus, a digital filtering function is used to restore the best MTF for the processed image according to the measured MTF. The use of this filter requires knowing the amount of defocus, which is being measured using any one of a number of available means. The filter used between defocus steps $\delta_F$ is the linear interpolation of the adjacent focus steps.

Figure 16:
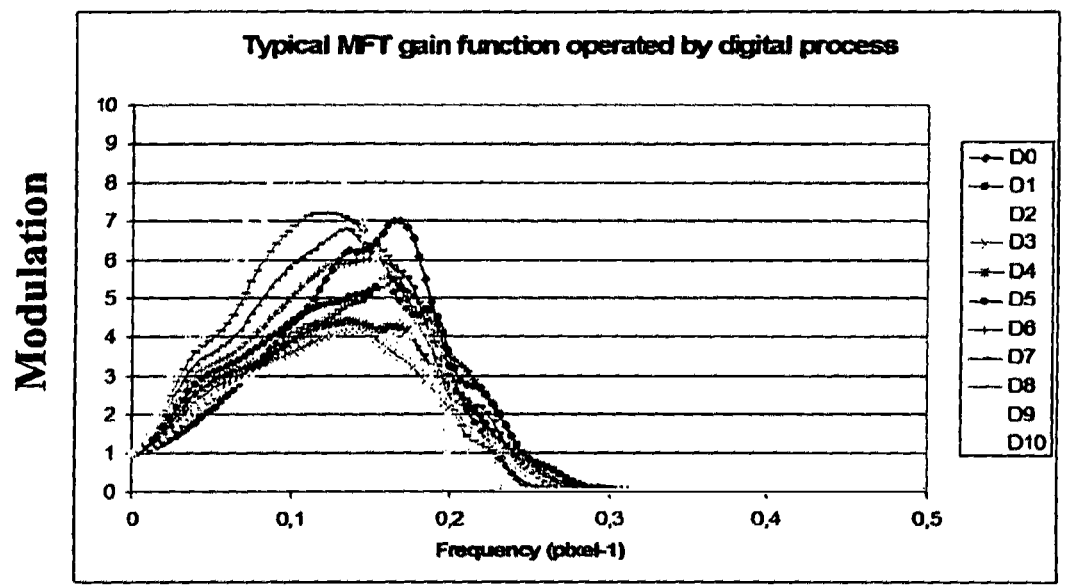
FIG. 16 is a plot for various defocus positions of the gain in the enhanced MTF as obtained from image processing as compared to the raw MTF.

FIG. 16 plots an example of a raw MTF and the restored (enhanced) MTF as obtained using the above-described filtering process. The raw MTF plots for different focus distances illustrate the MTF dispersion that occurs due to defocus.

MTF Restoration

The above-mentioned MTF gain function used to restore or enhance the raw MTF is a three-dimensional function given G(u, v, d), wherein u is the spatial frequency along X axis, v is the spatial frequency along Y axis, and d is the distance of the object in the allowed extended depth of field DOF (d thus corresponds to forehead distance $D_H$). The rotational symmetry of the PSF and MTF results in a simplified definition of the gain function, namely:

$$G'(\omega, d) \text{ with } \omega^2 = u^2 + v^2$$

The rotational symmetry also makes G'(ω, d) a real function instead of a complex function in the general case.

The "enhanced" or "restored" OTF' is defined as:

$$OTF'(u,v,d) = G(u,v,d) OTF(u,v,d)$$

where OTF is the Optical Transfer Function of the lens for incoherent light, OTF' is the equivalent OTF of the imaging system including the digital processing, and G is the aforementioned MTF gain function. The relation for the restored or "output" or "enhanced" MTF (i.e., MTF') based on the original or unrestored MTF is given by:

$$MTF'(\omega,d) = G'(\omega,d) MTF(\omega,d)$$

The after-digital process is optimized to deliver the same MTF at any distance in the range of the working depth of field DOF. This provides a constant image quality, independent forehead distance $D_H$, so long as $D_H$ is within the depth of field DOF of optical system 20. Because optical system 20 has an extended depth of field DOF due to the presence of spherical aberration, I-R system 10 can accommodate a relatively large variation in head position and still be able to capture suitable images for performing iris recognition. This leads to I-R system 10 having higher reliability and reduced recognition-error probability. The constant MTF through-focus also provides a great advantage when providing the same image quality at any distances in the extended depth of field DOF. The advantage is greater when this system is used both for image data recording in the database unit 90, and as well as for recognition purposes. This method also allows for providing a standardized image quality for iris recognition.

Figure 17:
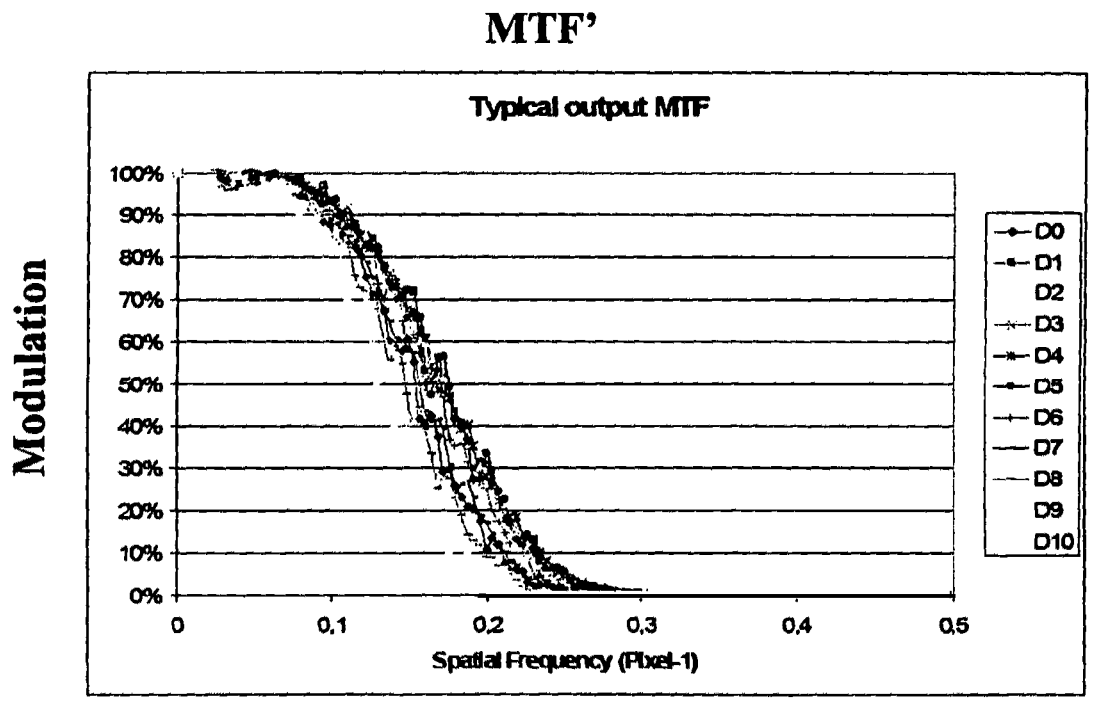
FIG. 17 plots for various defocus positions the typical "output" or enhanced MTF obtained after performing image processing.

FIG. 16 plots the typical output MTF through-focus gain obtained using the above-described process. Output MTF' is the product of the raw MTF and the gain function. FIG. 17 plots the typical output MTF' for the different focus positions. The shape of the output MTF' is close as possible of the hypergaussian function, namely:

$$MTF'(\omega, d) = \exp\left(-\left(\frac{\omega}{\omega_c}\right)^{2n}\right)$$

wherein n is the hypergaussian order, w is the cutoff frequency, which is set at the highest frequency where the raw MTF is higher that 5% on the whole range of the extended depth of field.

If n=1, the output MTF' is Gaussian. This provides a PSF, LSF (line-spread function) and ESF (edge-spread function) without any ringing of overshoot. If n>1, the output MTF' is a hypergaussian. For higher values of n, the contrast in high spatial frequencies is also high, but the occurrence of ringing and overshoot increases. A good compromise is n=2, wherein the output MTF' is well enhanced at low and medium spatial frequencies, while the ringing and overshoot are limited at 3%, which is acceptable for most biometric applications, including the present iris-recognition application.

The real output MTF' is as close as possible to a hypergaussian, and is determined by an optimization process that involves a merit function M, which is defined as:

$$M = A_0 \cdot \int_0^{Fc} \left( MTF'(\omega, d) - \exp\left(-\left(\frac{\omega}{\omega_c}\right)^{2n}\right)^2 \right) d\omega +$$
$$A_1 \cdot \int G'(\omega, d)^2 d\omega + A_2 \cdot \Delta os^2$$

Merit function M is minimized by using, for example, a Newton optimization algorithm. The first term with the coefficient A0 minimizes the deviation from the hypergaussain output MTF'. The second term with the coefficient A1 controls the power noise amplification. The third term with the coefficient A2 controls the overshoot amplification.

Figure 18:
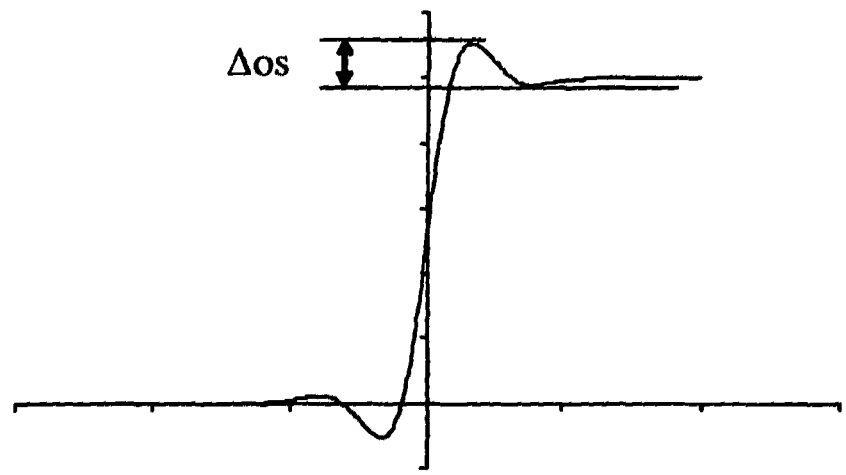
FIG. 18 is a plot of the intensity I vs. position for the image of an edge, showing the overshoot $\Delta os$ caused by ringing in the image.

It is important to control the power noise amplification. At distances where the gain on the raw MTF is higher in order to achieve the output MTF', a good compromise between the MTF level and the signal noise ratio on the image can be determined, while controlling the slope of the output MTF' at high special frequencies avoids significant overshoot. The third term in the merit function M is the square of the relative overshoot on an edge spread, which is illustrated in FIG. 18, wherein the overshoot is given by Δos.

Figure 19:
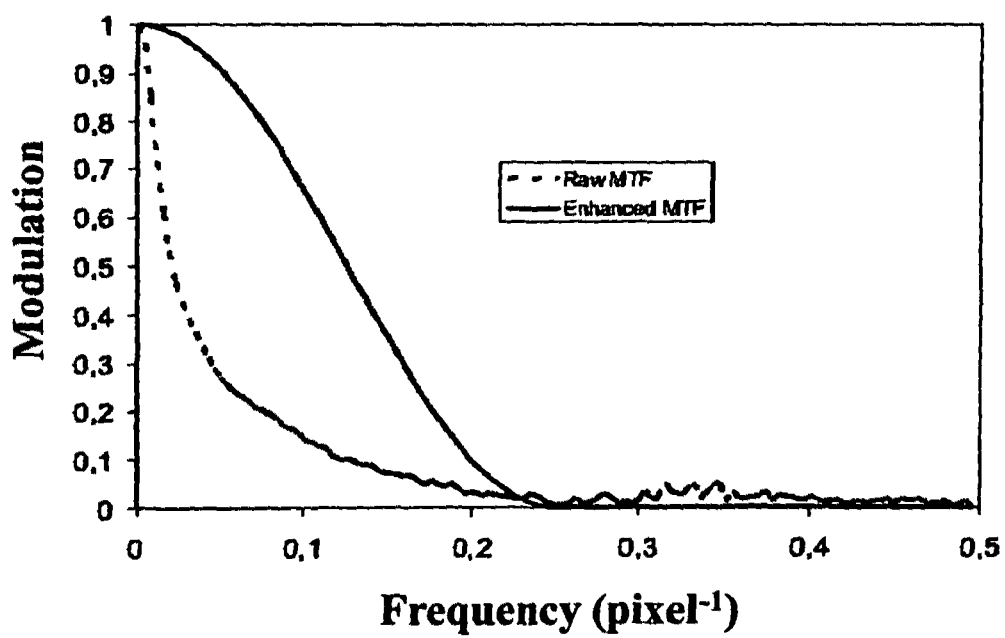
FIG. 19 plots the raw MTF and the enhanced (output) MTF at best focus to illustrate the recovery of image resolution via image processing.

FIG. 19 is a plot of the raw MTF along with an output MTF' formed using the process described above. The output MTF' has a smooth shape that avoids overshoots and other imaging artifacts. The applied gain of the digital filter is optimized or enhanced to obtain the maximum output MTF' while controlling the gain on noise.

In an example embodiment, the raw MTF is measured for calibration at different sampled distances that overlap the extended depth of field DOF by using a slanted edge with a uniform incoherent backlighting at the same spectrum used during image capture.

Image Capture

An example process for capturing an image 44' using I-R system 10 is as follows. First, a measurement of distance $D_H$ is performed as described above. This involves controller 50 activating laser 280 to create laser spot 80 on forehead 42 of person 35. If no laser spot 80 is detected, it is assumed that no person is located in the depth of field DOF and so no iris image is captured. The distance measurement is repeated until a person's head is detected.

Once laser spot 80 is detected, if forehead distance $D_H$ is in the allowed range as defined by the I-R systems depth of focus DOF, then the iris-measurement process continues. Otherwise, the person needs to reposition their head, and the forehead distance $D_H$ is measured again. Once the person's head is properly positioned, a face-region image 44' is then captured by activating illumination unit 60 to form illumination region 48 as described above. The timing of activating illumination unit 60 and the activation of image sensor 30 is coordinated via electronic signal S200 from controller 50 and signal $S_{PGO}$ from image sensor 30 so that the proper exposure is obtained. Photosensitive surface 32 then receives image 44' and converts it into the aforementioned raw digital electronic image represented by electrical signal SRI. This signal is provided to image processing unit 54 in controller 50 for subsequent image processing to form the processed image as embodied in a digital electronic image represented by electrical signal SPI, as described above.

Eye Location

The location of eyes 34L and 34R needs to be accurately established in order to speed up the digital imaging processing. Accurate eye locations allow determining two regions of interest where the digital process can be applied, as opposed to having to process the entire image 44'. Reducing the amount of pixels that need image processing simplifies the image processing and speeds up the image-processing computations.

Establishing the locations of the two eyes does not require the fine sampling needed for acquiring the multi-megapixel image 44'. For this purpose, the resolution of image 44' can be reduced (e.g., by a factor of 8) to produce an image captured by 375×276 pixels. In an example embodiment, image sensor 30 is capable of switching between low-resolution and high-resolution image-capture modes. The eye tracking is performed by locating two peaks P1 and P2 of a correlation function of the image with a standard average template. This template is a 32×32 matrix that reproduces the bright specular peak of reflection of the illumination beam on the cornea and the dark area of the pupil. This template matches very well to all eyes regardless of eye color.

Figure 20:
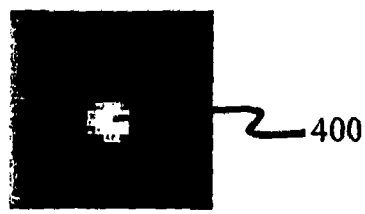
FIG. 20 is a photograph of the reflection from the eye of a spot used to perform eye location analysis.
Figure 21:
FIG. 21 is an image of the face region as taken by the I-R system of the present invention, wherein the image shows pronounced correlation peaks with standard eye template, which are used to perform eye location.
Figure 22:
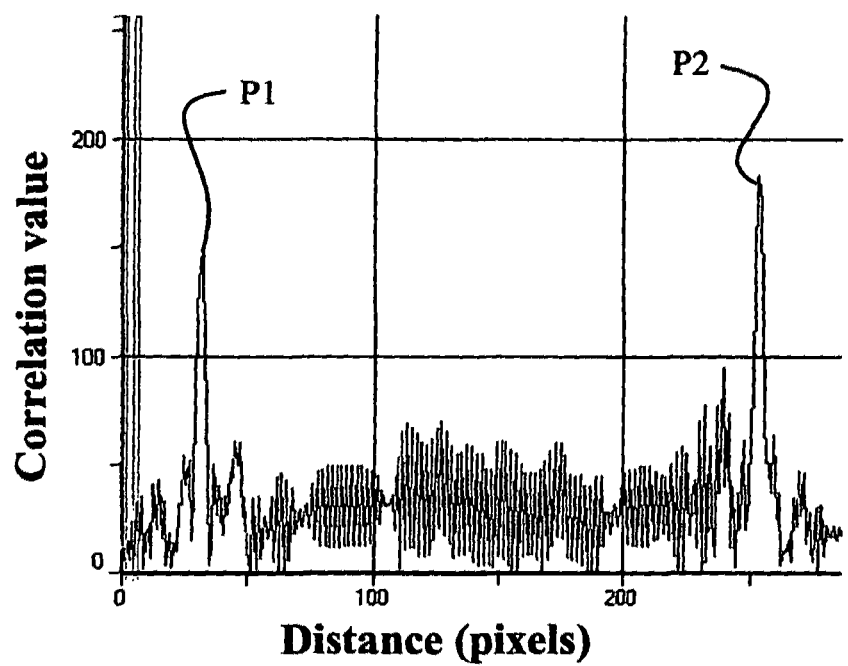
FIG. 22 plots the correlation function vs. distance, illustrating how the eye reflections show up as peaks PR and PL corresponding to reflections from the right and left eyes, respectively.

FIG. 20 is a picture showing the reflection 400 from an eye 34, while FIG. 21 is a face region image 44' correlated with a standard eye template that shows reflections 400 (the two white spots) from the left and right eyes. FIG. 22 is a correlation plot wherein the two peaks P1 and P2 that determine the two eye positions are well distinguished from the background. The two regions of interest for image processing can be reduced to two cropped images of 512×512 pixels each of the raw image centered on the two correlation peak positions P1 and P2.

Eye Motion Monitoring

Besides establishing the respective locations of the persons' two eyes, it is also necessary to monitor whether there is any motion in either or both eyes, such as from blinking or moving the eyes during the image acquisition process. In order to monitor eye motion, sequential images ("eye-motion images") are taken using two small regions of interest (e.g., 512×512 pixels) in image sensor 30. The number of sequential eye-motion images taken can be, for example, between 7 and 10 for each eye within 1 or 2 seconds.

If a blink is detected in the eye-motion images while taking capturing image 44', the particular iris measurement is canceled. If eye motion is detected in the eye-motion images, and the motion is greater than a tolerable threshold associated with image blur (which corresponds to a MTF degradation), then the particular iris measurement based on capturing image 44' is canceled.

On the other hand, if no blurring motion (or sub-threshold motion) and no blinking is detected, then the iris measurement process goes forward with captured image 44'.

Image Noise Reduction by Averaging Sequential Images

There are two distinct sources of noise associated with the image acquisition and image processing process. The first source of noise is called "fixed-pattern noise" or FP noise for short. The FP noise is reduced by a specific calibration of image sensor 30 at the operating conditions for iris imaging. In an example embodiment, this noise is reduced via a multi-level mapping of the fixed pattern noise. Each pixel is corrected by a calibration table, e.g., a lookup table that has the correction values. This requires an individual calibration of each image sensor and calibration data storage in a calibration file. The mapping of the fixed pattern noise for a given image sensor is performed, for example, by imaging a pure white image (e.g., from an integrating sphere) and measuring the variation in the image.

The other source of noise is shot noise, which is random noise. The shot noise is produced in electronic devices by the Poisson statistics associated with the movement of electrons. Shot noise also arises when converting photons to electrons via the photo-electric effect.

Imaging face region 44 to form face region image 44' requires a high-definition image sensor 30. As discussed above, in an example embodiment, image sensor 30 is or includes a CMOS or CCD camera having an array of 3000× 2208 pixels with a pixel size of 3.5 μm. The full well capacity is reduced to 21,000 electrons for a CMOS camera at this small pixel size, and the associated minimum of shot noise is about 43.2 dB at the saturation level.

An important aspect of the I-R system of the present invention includes approaches to reduce noise so that the MTF quality is improved, which leads to better iris-pattern images and better iris-recognition capability. The random nature of the shot noise is such that averaging N captured images is the only available approach to reducing the noise (i.e., improving the SNR). The noise decreases (i.e., the SNR increases) in proportion to $N^{1/2}$.

Figure 23:
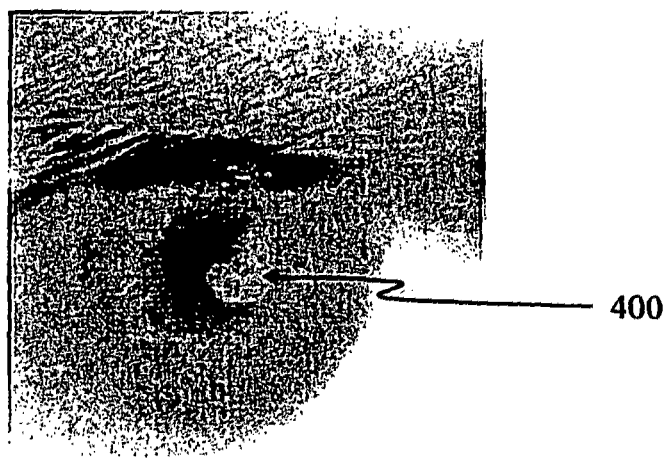
FIG. 23 is an image of the left eye showing image blur due to eye movement, and also showing the movement of the eye reflection.
Figure 24:
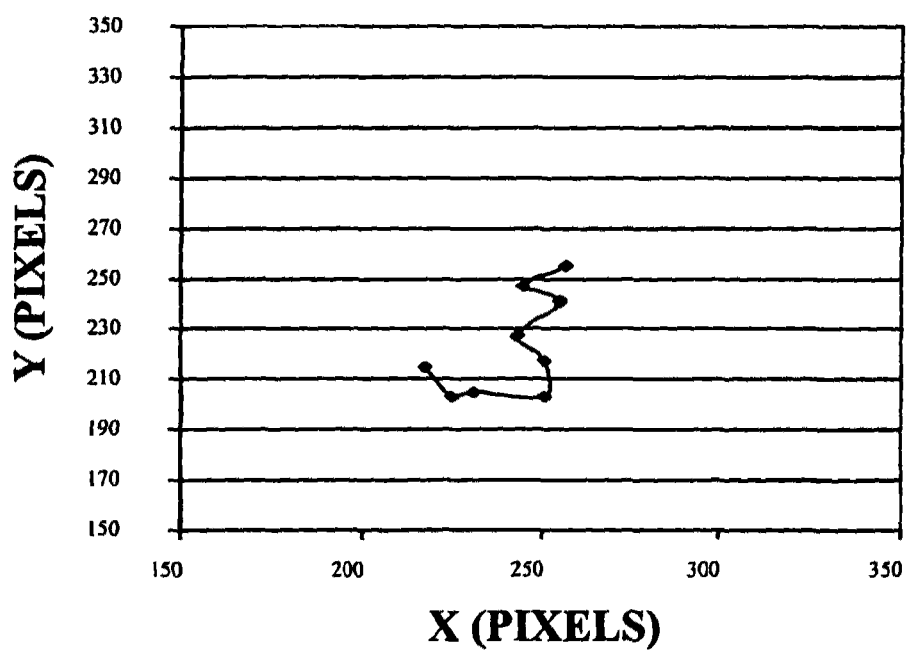
FIG. 24 is a plot of the pixel locations of the image of the eye reflection for a sequence of eye images, showing how the eye reflection moves along a measurable path during eye movement.

Averaging N captured images is a suitable noise reduction approach so long as the images being averaged are of a fixed object or scene. However, such averaging is problematic when the object moves, as is the case in the present iris-recognition application. Fortunately, the trajectory of a moving eye can be tracked and accurately measured. The averaging process for reducing noise can then be used by accounting for and compensating for any eye motion prior to averaging raw images 44'. FIG. 23 shows a portion of image 44' that shows eye movement as indicated by blurriness in the image, and in the movement of reflection 400. FIG. 24 plots the trajectory of the eye motion shown in FIG. 23 by tracking the location of reflection 400 for a sequence of eye images.

The image averaging process of the present invention uses a correlation function between the sequential images at the same region of interest. The relative two-dimensional image shifts are determined by the location of the correlation peak. The region of interest of the correlation is reduced to the pupil and iris area to avoid any disturbance due to eyelid motion. The correlation function is processed in the Fourier domain to speed the process by using a fast-Fourier transform (FFT) algorithm. The correlation function provided is sampled at the same sampling intervals as the initial images. The detection of the correlation maximum is accurate to the size of one pixel.

An improvement of this measurement technique is to use a 3×3 kernel of pixels centered on the pixel associated with the maximum correlation peak. The sub-pixel location is determined by fitting to two-dimensional parabolic functions to establish a maximum. The (X,Y) image shift is then determined. The images are re-sampled at their shifted locations. If the decimal part of the measured (X,Y) shift is not equal to 0, a bi-linear interpolation is performed. It is possible to use a Shannon interpolation as well because there is no signal in the image at frequencies higher than the Nyquist frequency. All the images are summed after being re-sampled, taking in account the (X,Y) shift in the measured correlation.

Blinking and Image Averaging

As discussed above, eye motion in the form of blinking, eye rotation and eye movement can adversely affect the image acquisition process and adversely affect the ability of the image processor to generate good processed iris images.

Figure 25:
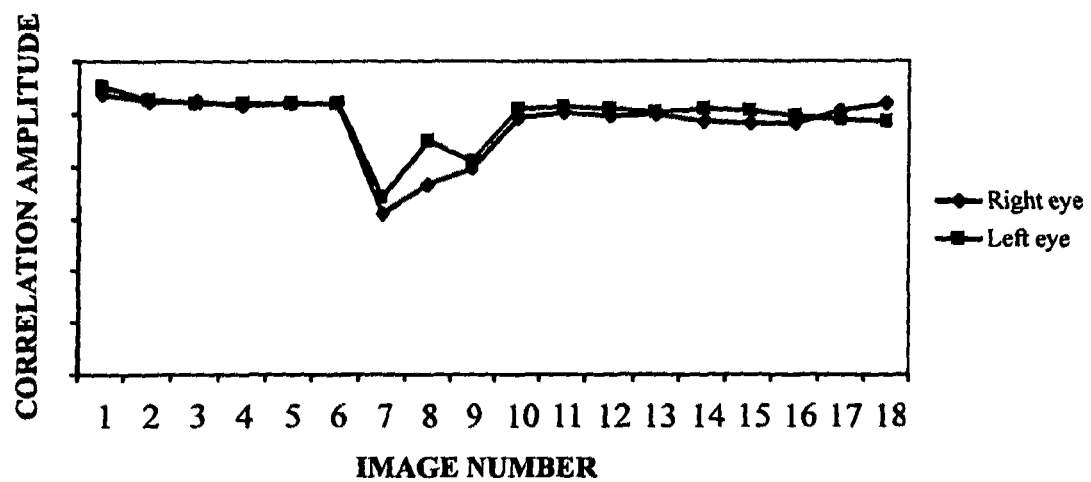
FIG. 25 is a plot of the correlation amplitude vs. image number, showing how the correlation changes when one or both eyes blink.

The correlation function peak has almost constant amplitude for adjacent acquired images except for a translation associated with the eye motion. A blink on the other hand is detected as a negative pulse in the correlation amplitude function on the group of sequential images. FIG. 25 plots the correlation amplitude vs. image number for the acquired images. A blink is indicated by the dip in the correlation amplitude that occurs between images 6 and 10.

If there are more than two images affected by blinking, the whole acquisition is rejected. If only two images are affected, the averaging process can be performed on those images not affected by blinking.

Eye Rotation and Image Averaging

Eye rotation produces a negative variation in the correlation amplitude function on the group of sequential images. The origin is the apparent translation of the iris pattern with eye rotation, wherein the specular reflection location moves less with the eye rotation because the axis of rotation is close to the center of curvature of the cornea It is thus best to reject all the images when such an event occurs and restart the image acquisition process.

Blur Motion and Image Averaging

Eye rotation can produce blurring when the distance the eye moved between images is relatively large. In an example embodiment, the allowed tolerance on eye motion is based on an exposure time of 20 ms. The MTF decrease is given by a Sinc function of the motion speed V and the exposure time T, namely:

$$MTF_{Blur\_attenuation} = \frac{\sin(\pi VT)}{\pi VT}$$

This expression can be used to set a threshold on MTF blur that occurs due to eye rotation.

Generalized Large Depth-of-Field Imaging

The present invention has been described above mainly in connection with an I-R system for the sake of illustration. However, it is also applicable to a number of other imaging applications, such as for cell phone cameras and image scanning, that require imaging an object that can vary in its position, or that has such axial depth that one portion of the object may be out of focus while another may be in focus if a conventional imaging system were to be used.

It will thus be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed is:

1. An iris-recognition (I-R) system for capturing images of one or both irises of a person over a large depth of field (DOF), comprising:

an illumination system adapted to i) illuminate at an imaging wavelength $\lambda_{IM}$ a facial region of the person, wherein the facial region includes one or both eyes and at least a forehead portion of the person, and ii) to form a spot on the forehead portion;

an optical system having an object plane within the large depth of field DOF, an image plane within a correspondingly large depth of focus DOF' with an image sensor arranged thereat, and an amount of spherical aberration (SA) at an imaging wavelength $\lambda_{IM}$ such that the depth of field DOF increases by an amount between 50% and 500% as compared to the optical system being diffraction limited, the optical system configured to form on the image sensor an image of the facial region when the facial region is placed within the depth of field DOF, wherein said facial region image includes an image of the forehead spot; and a controller electrically connected to the image sensor and to the illumination system, the controller adapted to control and coordinate the operation of the illumination system and the image sensor, and adapted to perform image-processing on the facial-region image to form an enhanced image of one or both irises based on an enhanced modulation transfer function (MTF) formed using forehead distance information obtained from the forehead spot.

2. The I-R system of claim 1, wherein the amount of spherical aberration SA satisfies at least one of the following relationships: i) $0.2\lambda_{IM} \le SA \le 5\lambda_{IM}$; ii) $0.2\lambda_{IM} \le SA \le 0.9\lambda_{IM}$; and iii) $0.2\lambda_{IM} \le SA \le 0.75\lambda_{IM}$.

3. The I-R system of claim 1, wherein the imaging wavelength $\lambda_{IM}$ satisfies the relationship 700 nm $\le \lambda_{IM} \le$ 900 nm.

4. The I-R system of claim 1, wherein the image sensor is adapted to form an electrical signal SRI representative of the raw facial image formed on the image sensor.

5. The I-R system of claim 4, wherein the controller includes an image-processing unit adapted to receive and process the electronic signal SRI to form an enhanced image of one or both irises that has a higher contrast than the raw image contrast.

6. The I-R system of claim 5, further including a database unit electronically connected to the image processor and adapted to retrievably store on a computer-readable medium at least one enhanced-contrast image.

7. The I-R system of claim 1, wherein the illumination system includes a first light source adapted to illuminate the facial region, and a second light source adapted to form the forehead spot.

8. The I-R system of claim 1, wherein the optical system consists of a single optical element and an aperture stop located at a position different from the single optical element.

9. The I-R system of claim 8, wherein the single optical element is a plano-convex lens wherein the plano surface faces objectwise.

10. The I-R system of claim 8, wherein the aperture stop is arranged imagewise of the lens in a position that minimizes comatic aberration.

11. The I-R system of claim 1, wherein the optical system includes an afocal or substantially afocal front lens group.

12. The I-R system of claim 1, wherein the optical system is configured so that the amount of spherical aberration can be adjusted by adjusting one or more surface radii of a single optical element in the front lens group.

13. A method of forming an enhanced image of at least one iris of a person, comprising:
  forming a raw image of a facial region of the person that includes at least one eye of the person and a forehead portion of the person using an optical system having an amount of spherical aberration that increases a depth of field (DOF) of the optical system by an amount between 50% and 500% as compared to the optical system being diffraction limited;
  using an image sensor, electronically capturing the raw image to form a digitized raw image, the raw image having a corresponding raw modulation transfer function (MTF);
  establishing an amount of defocus in the digitized raw image based on a position of the person relative to the optical system including determining the amount of defocus by forming a spot formed on the person's forehead portion and establishing the amount of defocus based on the location of the spot in the raw image;
  forming an enhanced MTF from the raw MTF by multiplying the raw MTF by a gain function, wherein the enhanced MTF is a function of the amount of defocus; and
  applying the enhanced MTF to the digitized raw image to obtain the enhanced image.

14. The method of claim 13, wherein the optical system consists of a single optical element and an aperture stop.

15. The method of claim 13, including increasing the DOF by up to an additional 20% by forming the single optical element from a glass type that adds chromatic aberration and while only reducing the average MTF by no more than about 25%.

16. The method of claim 13, including forming the single optical element from fused silica.

17. The method of claim 14, wherein the single optical element is one of a) a plano-convex lens, with its plano surface facing objectwise, b) a meniscus lens and c) a biconvex lens.

18. The method of claim 17, wherein the aperture stop is arranged imagewise of the lens in a position that minimizes comatic aberration.

19. The method of claim 13, wherein the optical system includes an afocal or a substantially afocal front lens group.

20. The method of claim 19, wherein the optical system is configured so that the amount of spherical aberration can be adjusted by adjusting one or more surface radii of a single optical element in the front lens group.

21. The method of claim 13, further including:
  illuminating the face portion with a first illumination beam that forms an illumination region corresponding to the face portion and a second illumination beam that forms that spot.

22. The method of claim 13, further including capturing a number N of raw images and analyzing said raw images to establish whether one or both eyes had eye motion and/or eye blinking.

23. The method of claim 22, including tracking said eye motion and accounting for said eye motion to identify regions of said image sensor to be used for forming the enhanced image.

24. The method of claim 22, including averaging the N images so as to reduce noise in the enhanced image.

25. The method of claim 13, including:
  measuring a distance between the person and the optical system; and
  wherein forming the enhanced MTF includes applying a two-dimensional linear digital filter to the raw MTF according to the measured distance.

26. The method of claim 24, including measuring the raw MTF at different sampled distances that overlap the depth of field DOF by using a slanted edge with uniform incoherent backlighting.

27. An enhanced depth of field (DOF) imaging system for forming an enhanced contrast image of an object, comprising:
  an optical system having an amount of spherical aberration (SA) at an imaging wavelength $\lambda_{IM}$ such that the depth of field DOF increases by an amount between 50% and 500% as compared to the optical system being diffraction limited, the optical system configured to form an image of the object at an image plane when the object is within the DOF and at a distance away from the optical system;
  an image sensor located at the image plane and adapted to form an electrical signal representative of the image as a raw image;

a controller electrically connected to the image sensor and adapted to receive the electrical signal and perform image-processing on the raw image to form an enhanced image using an enhanced modulation transfer function (MTF) formed based on said object distance further including an illumination system operably coupled to the controller and adapted to form a mark on the object that shows UP in the raw image, and wherein the controller is configured to determine the object distance based on a position of the mark in the raw image.

28. The imaging system of claim 27, wherein the controller is adapted to average N enhanced images to form a final enhanced image having reduced noise as compared to any of the N enhanced images.

29. The imaging system of claim 27, wherein the optical system consists of a single optical element and an aperture stop located at a position different from the single optical element.

30. The imaging system of claim 29, wherein the single optical element is one of a) a plano-convex lens wherein the plano surface faces objectwise, b) a meniscus lens, and c) a biconvex lens.

31. The imaging system of claim 29, wherein the aperture stop is arranged imagewise of the lens in a position that minimizes comatic aberration.

32. The imaging system of claim 27, wherein the optical system includes an afocal or substantially afocal front lens group.

33. The imaging system of claim 32, wherein the optical system is configured so that the amount of spherical aberration can be adjusted by adjusting one or more surface radii of a single optical element in the front lens group.

34. The imaging system of claim 27, wherein the mark is a spot.

35. The imaging system of claim 27, wherein:

the image sensor is adapted to switch between a low-resolution and a high-resolution image-capture mode; and wherein the controller is configured to track object motion by processing the low-resolution-mode raw image.

36. The imaging system of claim 35, wherein the object motion tracking is performed by locating at least one peak of a correlation function of the low-resolution-mode raw image relative to a reference location.

* * * * *

UNITED STATES PATENT AND TRADEMARK OFFICE
CERTIFICATE OF CORRECTION

| | | |
|---|---|---|
| PATENT NO. | : 8,594,388 B2 | Page 1 of 1 |
| APPLICATION NO. | : 12/450488 | |
| DATED | : November 26, 2013 | |
| INVENTOR(S) | : Mathieu | |

It is certified that error appears in the above-identified patent and that said Letters Patent is hereby corrected as shown below:

Title page, item (74) Attorney: Agent or Firm – after Downs Rachlin Martin PLCC, insert
-- Opticus IP Law PLLC --.

In the Claims

In column 23, claim 27, line 8, delete "UP" and insert -- up -- therefor.

Signed and Sealed this
Fifteenth Day of April, 2014

Michelle K. Lee
*Deputy Director of the United States Patent and Trademark Office*